(12) United States Patent
Zhang-Plasket et al.

(10) Patent No.: US 7,576,238 B2
(45) Date of Patent: Aug. 18, 2009

(54) PROCESS FOR THE PREPARATION OF SUBSTITUTED TETRALIN AND SUBSTITUTED INDANE DERIVATIVES

(75) Inventors: Fan Zhang-Plasket, Willow Grove, PA (US); Hua Zhong, Basking Ridge, NJ (US); Frank Villani, Perkasie, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/958,618

(22) Filed: Dec. 18, 2007

(65) Prior Publication Data

US 2008/0096962 A1   Apr. 24, 2008

Related U.S. Application Data

(63) Continuation of application No. 11/110,459, filed on Apr. 20, 2005, now abandoned.

(60) Provisional application No. 60/564,159, filed on Apr. 21, 2004.

(51) Int. Cl.
*C07C 381/00* (2006.01)
(52) U.S. Cl. .................. 562/428; 562/427; 562/426
(58) Field of Classification Search .............. None
See application file for complete search history.

(56) References Cited

U.S. PATENT DOCUMENTS

| | | | |
|---|---|---|---|
| 6,028,109 A | 2/2000 | Willson | |
| 6,306,854 B1 | 10/2001 | Brown et al. | |
| 6,750,236 B2 | 6/2004 | Urbahns et al. | |
| 7,351,857 B2 * | 4/2008 | Chen et al. ........ | 562/439 |
| 2002/0169192 A1 | 11/2002 | Hayward et al. | |
| 2003/0013729 A1 | 1/2003 | Iqbal et al. | |
| 2003/0032671 A1 | 2/2003 | Urbahns et al. | |

FOREIGN PATENT DOCUMENTS

| | | |
|---|---|---|
| EP | 399422 A1 | 11/1990 |
| EP | 1285908 A1 | 2/2003 |
| WO | WO 92/01068 A1 | 6/1992 |
| WO | WO 95/04713 A1 | 2/1995 |
| WO | WO 97/36579 A1 | 10/1997 |
| WO | WO 02/028821 A2 | 4/2002 |
| WO | WO 02/0064146 A1 | 8/2002 |
| WO | WO 02/0064549 A1 | 8/2002 |
| WO | WO 02/0100836 A2 | 12/2002 |
| WO | WO 2004/037777 A1 | 5/2004 |
| WO | WO 2004/037778 A1 | 5/2004 |
| WO | WO 2004/037779 A1 | 5/2004 |

OTHER PUBLICATIONS

Berge et al. Journal of Pharmaceutical Sciences, 1977 vol. 66(1) p. 1-19.*
Assismacopoulos-Jeannet, F. et al. "Effect of a peroxisome proliferator on β-oxidation and overall energy balance in obese (fa/fa) rats". *America Phy. Soc.*, 1991, pp. R278-R283.
Kliewer, S. A. et al., "Fatty acids and eicosanoids regulate gene expression through direct interactions with peroxisome prolideratior-activated receptors α and γ." *Proc. Natl. Acad. Sci.*, 1997, vol. 94, pp. 4318-4323.
Cecchi, R. et al., "Synthesis and β-adrenergic activity of atypical β-adrenergic phenylethanolaminotetralin stereoisomers." *Eur. J. Med Chem.* 1994, vol. 29, pp. 259-267.
Brown, P. J. et al., "Identification of peroxisome proliferators-activated receptor ligands from a biased chemical library", *Chem. & Bio.*, 1997, vol. 4, No. 12, pp. 909-918.
Brown, P. J. et al., "Generation of Secondary Alkyl Amines on Solid Support by Borane Reduction: Application to the Parallel Synthesis of PPAR Ligands", *Synthesis*, 1997, pp. 778-782.
Hawke, R. L., et al., "Potent pypocholesterolemic activity of novel ureido phenoxyisobutyrates correlates with their Intrinsic fibrate potency and not with their ACAT inhibitory activity." *J. Lipid Res.*, 1997, vol. 38, pp. 1189-1203.
Brown, P. J., "A Ureido-Thioisobutyric Acid (GW9578) Is a Subtype-Selective PPAR α Agonist with Potent Lipid-Lowering Activity." *J. Med. Chem.*, 1999, vol. 42, pp. 3785-3788.
Guerre-Millo, M. et al., "Peroxisome Proliferator-activated Receptor α Activators Improve Insulin Sensitivity and Reduce Adiposity." *J. Bio. Chem.*, 2000, vol. 275, No. 22, pp. 16638-16642.
Brown, P. J., "Identification of a Subtype Selective Human PPAR α Agonist Through Parallel-Array Synthesis." *Bioorg. Med. Chem. Lett.*, 2001, vol. 11, pp. 1225-1227.
PCT International Search Report dated Sep. 28, 2005 for PCT Application No. PCT/US2005/013870, which relates to U.S. Appl. No. 11/958,618, filed herewith.

* cited by examiner

*Primary Examiner*—Paul A Zucker
*Assistant Examiner*—Yevegeny Valenrod
(74) *Attorney, Agent, or Firm*—Evelyn D. Shen; Jeremy K. McKown

(57) ABSTRACT

The present invention relates to novel processes for the preparation of substituted tetralin and substituted indane derivatives. The present invention is further directed to novel processes for the preparation of intermediates in the preparation of the substituted tetralin and substituted indane derivatives.

4 Claims, No Drawings

US 7,576,238 B2

PROCESS FOR THE PREPARATION OF SUBSTITUTED TETRALIN AND SUBSTITUTED INDANE DERIVATIVES

CROSS REFERENCE TO RELATED APPLICATION

This application is a continuation of U.S. application Ser. No. 11/110,459, filed Apr. 20, 2005 now abandoned, which claims the benefit of U.S. Provisional Application No. 60/564,159, filed Apr. 21, 2004, the contents of which are hereby incorporated by reference.

FIELD OF THE INVENTION

The present invention relates to a novel processes for the preparation of substituted tetralin and substituted indane derivatives. The substituted tetralin and substituted indane derivatives are PPAR alpha agonists, useful for elevating serum levels of high density lipoproteins (HDL), improving levels of intermediate density lipoproteins (IDL), and lowering serum levels of triglycerides, low density lipoproteins (LDL), atherogenic molecules, and/or free fatty acids (FFA). The substituted tetralin and substituted indane compounds are further useful in treating hypertriglyceridemia, raising levels of HDL, lowering levels of LDL, and/or lowering total cholesterol. The present invention is further directed to novel processes for the preparation of intermediates in the preparation of the substituted tetralin and substituted indane derivatives.

SUMMARY OF THE INVENTION

The present invention is directed to novel processes for the preparation of substituted tetralin and substituted indane derivatives. The substituted tetralin and substituted indane derivatives and their use for the treatment of PPAR alpha-mediated diseases including, but not limited to dyslipidemia, cardiovascular disorders, impaired glucose tolerance, hyperinsulinemia, hyperglycemia, insulin resistance, early, intermediate or late Type II diabetes (NIDDM), complications thereof and/or Syndrome X are disclosed in U.S. patent application Ser. No. 10/688,380, filed Oct. 17, 2003, U.S. patent application Ser. No. 10/688,379, filed Oct. 17, 2003 and U.S. patent application Ser. No. 10/688,572 filed Oct. 17, 2003, which are incorporated by reference herein in their entirety.

The present invention is directed to a process for the preparation of compounds of formula (L)

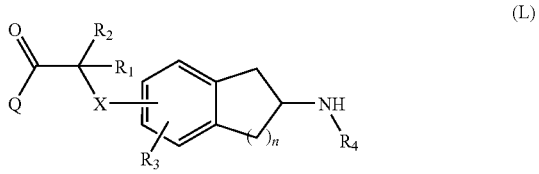

(L)

wherein

Q is selected from the group consisting of OH, $OPg^2$, $NH_2$ and $N(Pg^3Pg^4)$; wherein $Pg^2$ is a carboxylic acid protecting group; and wherein $Pg^3$ and $Pg^4$ are each independently selected from hydrogen, $C_{1-8}$alkyl, $C_{3-8}$cycloalkyl or aryl; or $Pg^3$ and $Pg^4$ are taken together with the nitrogen atom to which they are bound to form $C_{3-10}$heteroaryl or $C_{3-10}$non-aromatic heterocyclic;

each of $R_1$ and $R_2$ is independently H, $C_{1-6}$alkyl, $(CH_2)_m NR_a R_b$, $(CH_2)_m OR_8$, $(CH_2)_m NH(CO)R_8$ or $(CH_2)_m CO_2 R_8$;

wherein each of $R_a$, $R_b$, and $R_8$ is independently H or $C_{1-6}$alkyl; and m is an integer from 1 to 6;

alternatively, $R_1$ and $R_2$ are taken together with the carbon atom to which they are attached to form a $C_{3-7}$cycloalkyl;

n is an integer from 1 to 2;

X is S;

provided that when n is 1, X is bound at the 5 or 6 position; and when n is 2, X is bound at the 6 or 7 position; provided further that when n is 2 and X is bound at the 6 position, then $R^3$ is other than hydrogen and bound at the 7 position;

$R_3$ is H, $C_{1-3}$alkoxy, $C_{1-3}$alkylthio, halo, $C_{1-6}$alkyl, $NR_9 R_{10}$, $NHCOR_{10}$, $CONHR_{10}$ or $COOR_{10}$; and $R_3$ is ortho or meta to X; provided that $R_3$ is other than $CF_3$;

each $R_9$ and $R_{10}$ is independently $C_{1-6}$alkyl;

$R_4$ is H or —$(C_{1-5}$straight chain alkylene$)R_{15}$; wherein $R_{15}$ is H, $C_{1-7}$alkyl, [di($C_{1-2}$alkyl)amino]($C_{1-6}$alkylene)-, ($C_{1-3}$alkoxyacyl)($C_{1-6}$alkylene)-, $C_{1-6}$alkoxy, $C_{3-7}$alkenyl or $C_{3-8}$alkynyl;

wherein $R_4$ has no more than 9 carbon atoms;

alternatively, $R_4$ is -(straight chain $C_{1-5}$alkylene)$R_{16}$; wherein $R_{16}$ is $C_{3-6}$cycloalkyl or a 5-6 membered non-aromatic heterocyclyl with between 1 and 2 heteroatoms selected from N, O, and S;

wherein each of the above hydrocarbyl and heterocarbyl moieties may be optionally substituted with between 1 and 3 substituents independently selected from F, Cl, Br, I, amino, methyl, ethyl, hydroxy or methoxy;

comprising

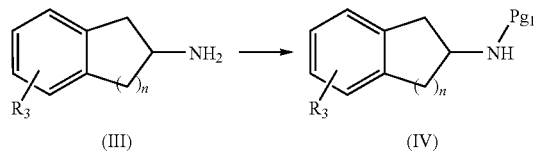

reacting a compound of formula (III), to yield the corresponding compound of formula (IV), wherein $Pg^1$ is a nitrogen protecting group which is inert to $ClSO_3H$;

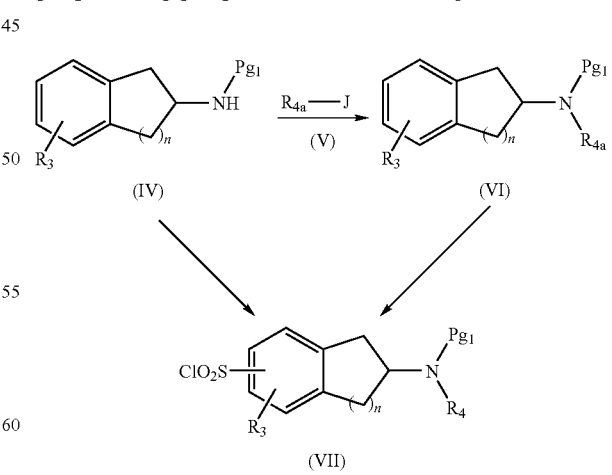

reacting the compound of formula (IV) with a suitably substituted compound of formula (V) wherein $R_{4a}$ is $R_4$ other than hydrogen and wherein J is Br, Cl or I, in the presence of a base, to yield the corresponding compound of formula (VI);

and then reacting the compound of formula (VI) with ClSO$_3$H, to yield the corresponding compound of formula (VII);

alternatively, reacting the compound of formula (IV) with ClSO$_3$H, to yield the corresponding compound of formula (VII) wherein R$_4$ is hydrogen;

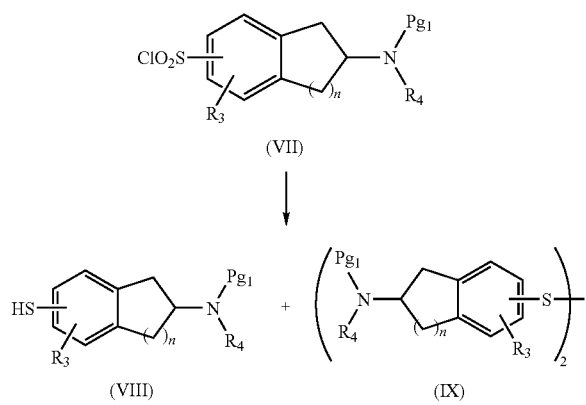

(VII)

(VIII)       (IX)

reacting the compound of formula (VII) with a reducing agent capable of reducing the chlorosulfonyl group on the compound of formula (VII), to yield a mixture of the corresponding compound of formula (VIII) and the corresponding compound of formula (IX);

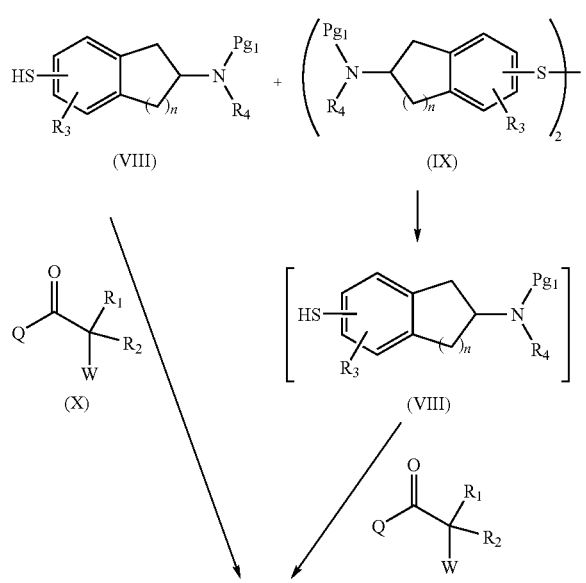

(VIII)       (IX)

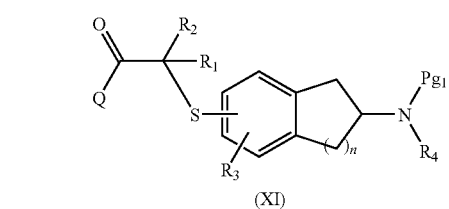

(X)       (VIII)

(X)

(XI)

reacting the compound of formula (VIII), isolated or in a mixture with the compound of formula (IX), with a suitably substituted compound of formula (X), wherein W is Br, Cl or I, in the presence of a base, to yield the corresponding compound of formula (XI);

alternatively, reacting the compound of formula (IX), isolated or in a mixture with the compound of formula (VIII), with a reducing agent capable of reducing the disulfide on compound of formula (IX), to yield the corresponding compound of formula (VIII); and then reacting the compound of formula (VIII) with a suitably substituted compound of formula (X), wherein W is Br, Cl or I, in the presence of a base, to yield the corresponding compound of formula (XI);

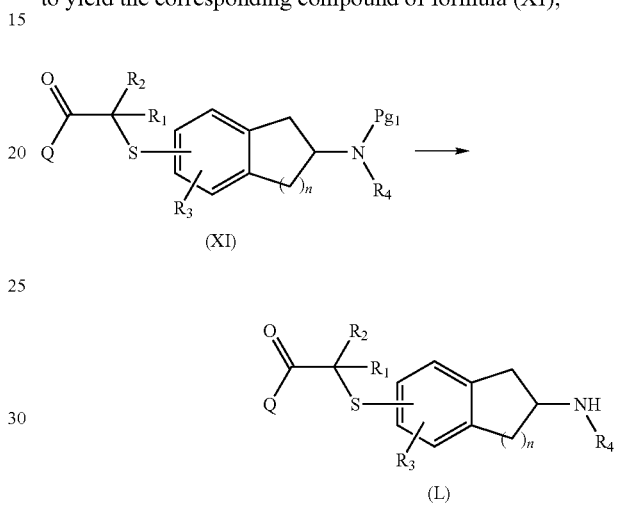

(XI)

(L)

reacting the compound of formula (XI), to yield the corresponding compound of formula (L).

The present invention is further directed to a process for the preparation of compounds of formula (L)

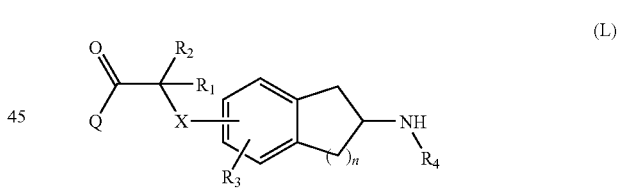

(L)

wherein

Q is selected from the group consisting of OH, OPg$^2$, NH$_2$ and N(Pg$^3$Pg$^4$); wherein Pg$^2$ is a carboxylic acid protecting group; and wherein Pg$^3$ and Pg$^4$ are each independently selected from hydrogen, C$_{1-8}$alkyl, C$_{3-8}$cycloalkyl or aryl; or Pg$^3$ and Pg$^4$ are taken together with the nitrogen atom to which they are bound to form C$_{3-10}$heteroaryl or C$_{3-10}$non-aromatic heterocyclic;

each of R$_1$ and R$_2$ is independently H, C$_{1-6}$alkyl, (CH$_2$)$_m$NR$_a$R$_b$, (CH$_2$)$_m$OR$_8$, (CH$_2$)$_m$NH(CO)R$_8$ or (CH$_2$)$_m$CO$_2$R$_8$;

wherein each of R$_a$, R$_b$, and R$_8$ is independently H or C$_{1-6}$alkyl; and m is an integer from 1 to 6;

alternatively, R$_1$ and R$_2$ are taken together with the carbon atom to which they are attached to form a C$_{3-7}$cycloalkyl;

n is an integer from 1 to 2;

X is S;

provided that when n is 1, X is bound at the 5 or 6 position; and when n is 2, X is bound at the 6 or 7 position; provided further that when n is 2 and X is bound at the 6 position, then $R^3$ is other than hydrogen and bound at the 7 position;

$R_3$ is H, $C_{1-3}$alkoxy, $C_{1-3}$alkylthio, halo, $C_{1-6}$alkyl, $NR_9R_{10}$, $NHCOR_{10}$, $CONHR_{10}$, or $COOR_{10}$; and $R_3$ is ortho or meta to X; provided that $R_3$ is other than $CF_3$;

each $R_9$ and $R_{10}$ is independently $C_{1-6}$alkyl;

$R_4$ is H or —($C_{1-5}$straight chain alkylene)$R_{15}$; wherein $R_{15}$ is H, $C_{1-7}$alkyl, [di($C_{1-2}$alkyl)amino]($C_{1-6}$alkylene)-, ($C_{1-3}$alkoxyacyl)($C_{1-6}$alkylene)-, $C_{1-6}$alkoxy, $C_{3-7}$alkenyl or $C_{3-8}$alkynyl;

wherein $R_4$ has no more than 9 carbon atoms;

alternatively, $R_4$ is -(straight chain $C_{1-5}$alkylene)$R_{16}$; wherein $R_{16}$ is $C_{3-6}$cycloalkyl or a 5-6 membered non-aromatic heterocyclyl with between 1 and 2 heteroatoms selected from N, O, and S;

wherein each of the above hydrocarbyl and heterocarbyl moieties may be optionally substituted with between 1 and 3 substituents independently selected from F, Cl, Br, I, amino, methyl, ethyl, hydroxy or methoxy;

comprising

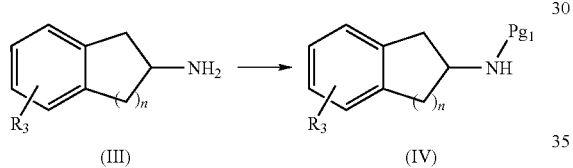

(III)      (IV)

reacting a compound of formula (III), to yield the corresponding compound of formula (IV), wherein $Pg^1$ is a nitrogen protecting group which is inert to $ClSO_3H$;

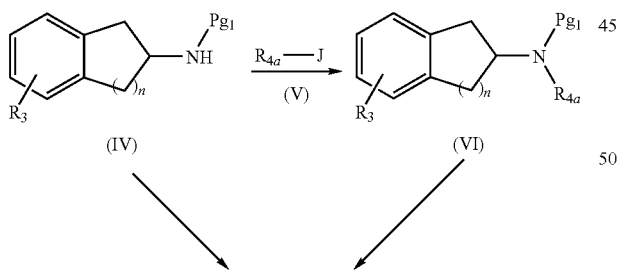

(IV)      (VI)

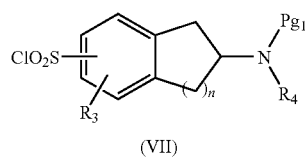

(VII)

reacting the compound of formula (IV) with a suitably substituted compound of formula (V) wherein $R_{4a}$ is $R_4$ other than hydrogen and wherein J is Br, Cl or I, in the presence of a base, to yield the corresponding compound of formula (VI); and then reacting the compound of formula (VI) with $ClSO_3H$, to yield the corresponding compound of formula (VII);

alternatively, reacting the compound of formula (IV) with $ClSO_3H$, to yield the corresponding compound of formula (VII) wherein $R_4$ is hydrogen;

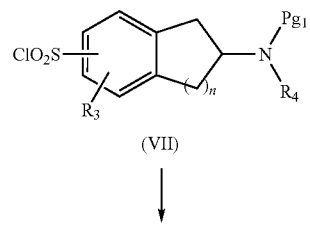

(VII)

↓

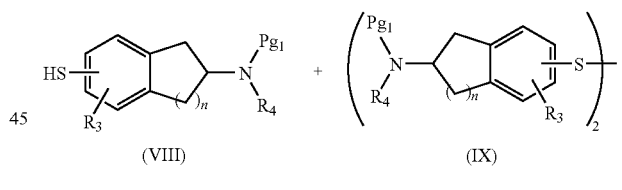

(VIII)      (IX)

reacting the compound of formula (VII) with a reducing agent capable of reducing the chlorosulfonyl group on the compound of formula (VII), to yield a mixture of the corresponding compound of formula (VIII) and the corresponding compound of formula (IX);

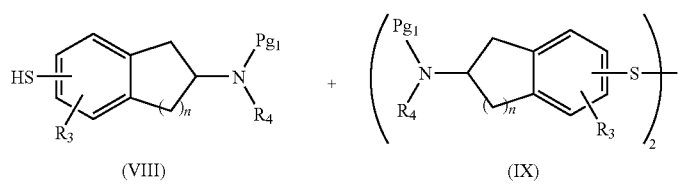

(VIII)      (IX)

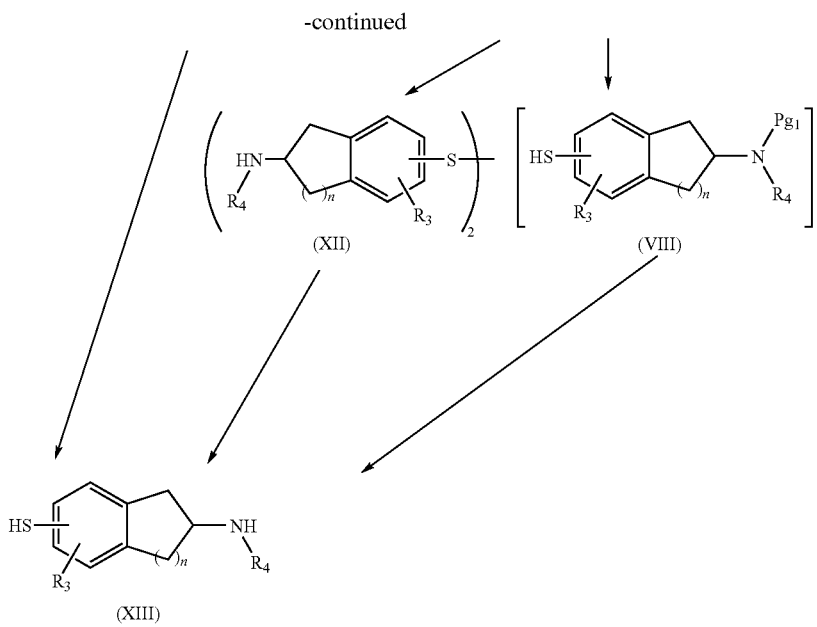

de-protecting the compound of formula (VIII), isolated or in a mixture with the compound of formula (IX), to yield the corresponding compound of formula (XIII);

alternatively, de-protecting the compound of formula (IX), isolated or in a mixture with the compound of formula (VIII), to yield a corresponding compound of formula (XII); and then reducing the compound of formula (XII) with a reducing agent capable of reducing the disulfide on compound of formula (XII), to yield the corresponding compound of formula (XIII);

alternatively still, reacting the compound of formula (IX), isolated or in a mixture with the compound of formula (VIII), with a reducing agent capable of reducing the disulfide on compound of formula (IX), to yield the corresponding compound of formula (VIII); and then de-protecting the compound of formula (VIII), to yield the corresponding compound of formula (XIII);

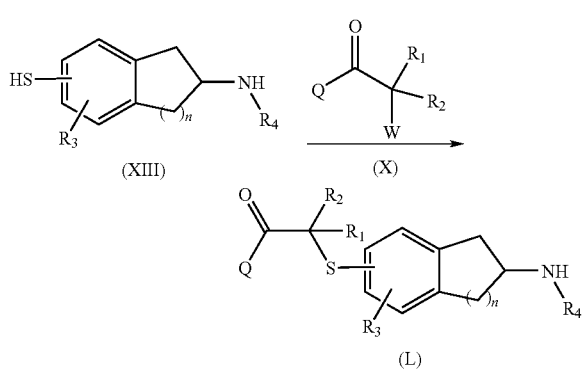

reacting the compound of (XIII) with a suitably substituted compound of formula (X), wherein W is Br, Cl or I, in the presence of a base, to yield the corresponding compound of formula (L).

The present invention is further directed to a process for the preparation of compounds of formula (L)

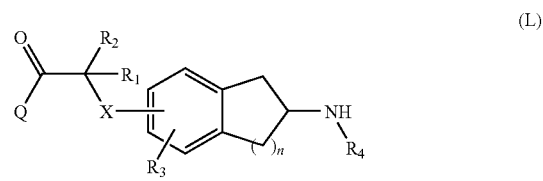

wherein

Q is selected from the group consisting of OH, $OPg^2$, $NH_2$ and $N(Pg^3Pg^4)$; wherein $Pg^2$ is a carboxylic acid protecting group; and wherein $Pg^3$ and $Pg^4$ are each independently selected from hydrogen, $C_{1-8}$alkyl, $C_{3-8}$cycloalkyl or aryl; or $Pg^3$ and $Pg^4$ are taken together with the nitrogen atom to which they are bound to form $C_{3-10}$heteroaryl or $C_{3-10}$non-aromatic heterocyclic;

each of $R_1$ and $R_2$ is independently H, $C_{1-6}$alkyl, $(CH_2)_m NR_aR_b$, $(CH_2)_m OR_8$, $(CH_2)_m NH(CO)R_8$ or $(CH_2)_m CO_2R_8$; wherein each of $R_a$, $R_b$, and $R_8$ is independently H or $C_{1-6}$alkyl; and m is an integer from 1 to 6;

alternatively, $R_1$ and $R_2$ are taken together with the carbon atom to which they are attached to form a $C_{3-7}$cycloalkyl;

n is an integer from 1 to 2;

X is S;

provided that when n is 1, X is bound at the 5 or 6 position; and when n is 2, X is bound at the 6 or 7 position; provided further that when n is 2 and X is bound at the 6 position, then $R^3$ is other than hydrogen and bound at the 7 position;

$R_3$ is H, $C_{1-3}$alkoxy, $C_{1-3}$alkylthio, halo, $C_{1-6}$alkyl, $NR_9R_{10}$, $NHCOR_{10}$, $CONHR_{10}$ or $COOR_{10}$; and $R_3$ is ortho or meta to X; provided that $R_3$ is other than $CF_3$;

each $R_9$ and $R_{10}$ is independently $C_{1-6}$alkyl;

$R_4$ is —($C_{1-5}$straight chain alkylene)$R_{15}$; wherein $R_{15}$ is H, $C_{1-7}$alkyl, [di($C_{1-2}$alkyl)amino]($C_{1-6}$alkylene)-, ($C_{1-3}$alkoxyacyl)($C_{1-6}$alkylene)-, $C_{1-6}$alkoxy, $C_{3-7}$alkenyl or $C_{3-8}$alkynyl;

wherein $R_4$ has no more than 9 carbon atoms;

alternatively, $R_4$ is -(straight chain $C_{1-5}$alkylene)$R_{16}$; wherein $R_{16}$ is $C_{3-6}$cycloalkyl or a 5-6 membered non-aromatic heterocyclyl with between 1 and 2 heteroatoms selected from N, O, and S;

wherein each of the above hydrocarbyl and heterocarbyl moieties may be optionally substituted with between 1 and 3 substituents independently selected from F, Cl, Br, I, amino, methyl, ethyl, hydroxy or methoxy;

comprising

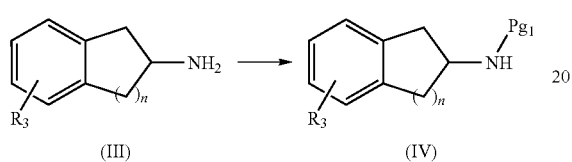

(III)　　　　　(IV)

reacting a compound of formula (III), to yield the corresponding compound of formula (IV), wherein $Pg^1$ is a nitrogen protecting group which is inert to $ClSO_3H$;

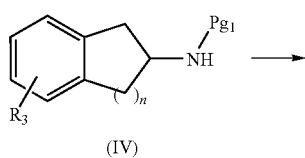

(IV)

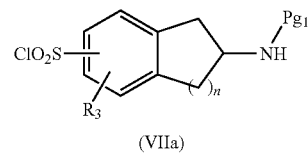

(VIIa)

reacting the compound of formula (IV) with $ClSO_3H$, to yield the corresponding compound of formula (VIIa);

(VIIa)

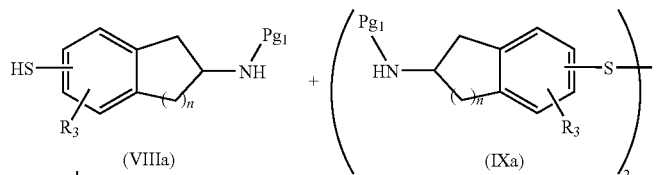

(VIIIa)　　　　　(IXa)

reacting the compound of formula (VIIa) with a reducing agent capable of reducing the chlorosulfonyl group on the compound of formula (VIIa), to yield a mixture of the corresponding compound of formula (VIIIa) and the corresponding compound of formula (IXa);

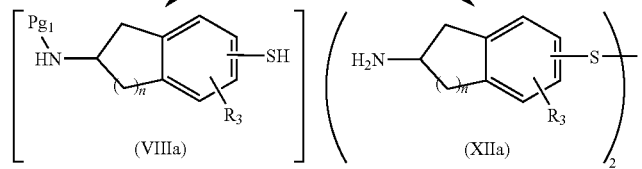

(VIIIa)　　　　　(IXa)

(VIIIa)　　　　　(XIIa)

-continued

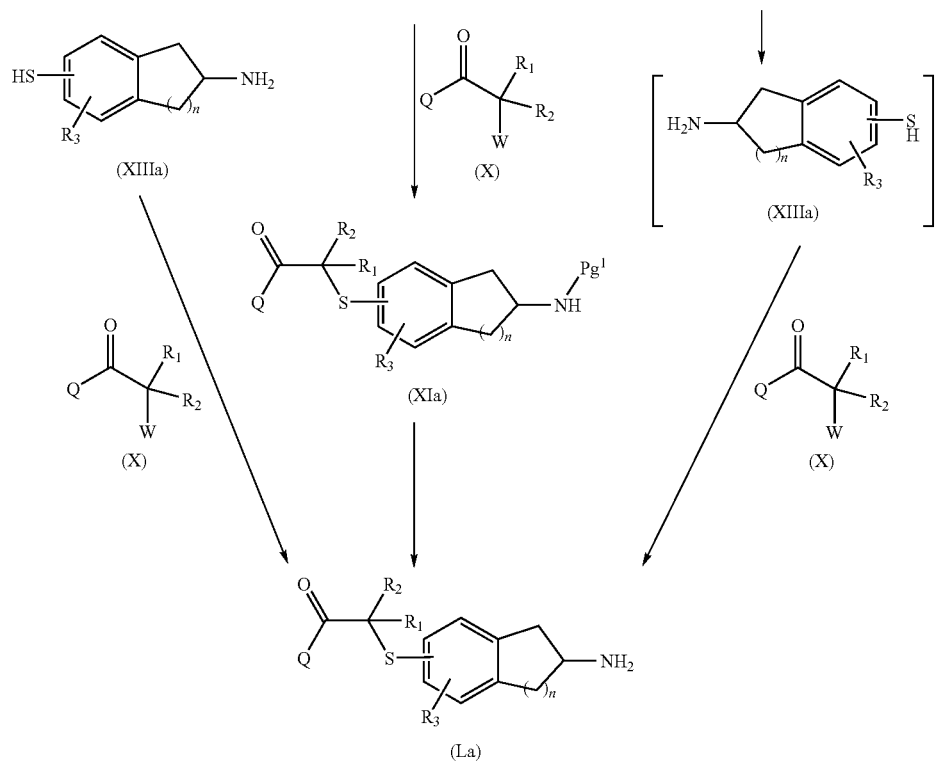

de-protecting the compound of formula (VIIIa), isolated or in a mixture with the compound of formula (IXa), to yield the corresponding compound of formula (XIIIa); and then reacting the compound of formula (XIIIa) with a suitably substituted compound of formula (X), wherein W is Cl, Br or I, in the presence of a base, to yield the corresponding compound of formula (La);

alternatively, reacting the compound of formula (IXa), isolated or in a mixture with the compound of formula (VIIIa), with a reducing agent capable of reducing the disulfide on the compound of formula (IXa), to yield the corresponding compound of formula (VIIIa); then reacting the compound of formula (VIIIa) with a suitably substituted compound of formula (X) wherein W is Br, Cl or I, in the presence of a base, to yield the corresponding compound of formula (XIa); and then reacting the compound of formula (XIa), to yield the corresponding compound of formula (La);

alternatively still, de-protecting the compound of formula (IXa), isolated or in a mixture with the compound of formula (VIIIa), to yield the corresponding compound of formula (XIIa); then reacting the compound of formula (XIIa) with a reducing agent capable of reducing the disulfide on the compound of formula (XIIa), to yield the corresponding compound of formula (XIIIa); and then reacting the compound of formula (XIIIa) with a suitably substituted compound of formula (X) wherein W is Br, Cl or I, in the presence of a base, to yield the corresponding compound of formula (La);

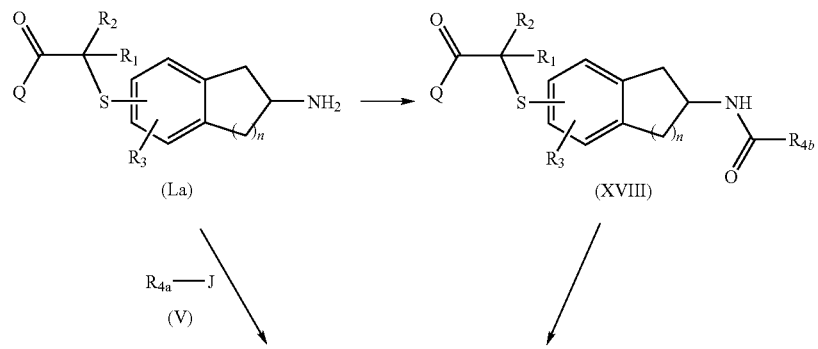

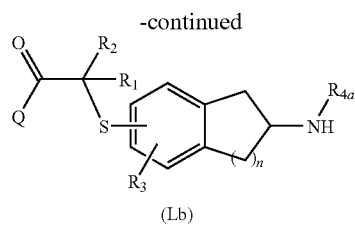

(Lb)

reacting the compound of formula (La) with a suitably substituted compound of formula (V) wherein $R_{4a}$ is $R_4$ other than hydrogen and wherein J is Br, Cl or I, to yield the corresponding compound of formula (Lb);

alternatively, reacting the compound of formula (La) with a suitably substituted acylating agent capable of attaching an —C(O)—$R_{4b}$ group onto the nitrogen of the compound of formula (La), wherein $R_{4b}$ is selected from ($C_{1-4}$ straight chain alkylene)$R_{15}$ or (straight chain $C_{1-4}$alkylene)$R_{16}$, in the presence of a base, to yield the corresponding compound of formula (XVIII); and then reacting the compound of formula (XVIII) with a reducing agent capable of reducing the amide on the compound of formula (XVIII), to yield the corresponding compound of formula (Lb).

The present invention is further directed to a process for the preparation of compounds of formula (Lc)

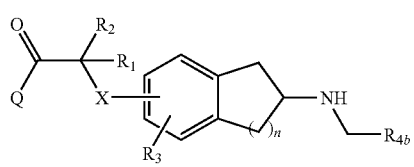

(Lc)

wherein

Q is selected from the group consisting of OH, $OPg^2$, $NH_2$ and $N(Pg^3Pg^4)$; wherein $Pg^2$ is a carboxylic acid protecting group; and wherein $Pg^3$ and $Pg^4$ are each independently selected from hydrogen, $C_{1-8}$alkyl, $C_{3-8}$cycloalkyl or aryl; or $Pg^3$ and $Pg^4$ are taken together with the nitrogen atom to which they are bound to form $C_{3-10}$heteroaryl or $C_{3-10}$non-aromatic heterocyclic;

each of $R_1$ and $R_2$ is independently H, $C_{1-6}$alkyl, $(CH_2)_m NR_aR_b$, $(CH_2)_mOR_8$, $(CH_2)_mNH(CO)R_8$ or $(CH_2)_mCO_2R_8$;

wherein each of $R_a$, $R_b$, and $R_8$ is independently H or $C_{1-6}$alkyl; and m is an integer from 1 to 6;

alternatively, $R_1$ and $R_2$ are taken together with the carbon atom to which they are attached to form a $C_{3-7}$cycloalkyl;

n is an integer from 1 to 2;

X is S;

provided that when n is 1, X is bound at the 5 or 6 position; and when n is 2, X is bound at the 6 or 7 position; provided further that when n is 2 and X is bound at the 6 position, then $R^3$ is other than hydrogen and bound at the 7 position;

$R_3$ is H, $C_{1-3}$alkoxy, $C_{1-3}$alkylthio, halo, $C_{1-6}$alkyl, $NR_9R_{10}$, $NHCOR_{10}$, $CONHR_{10}$ or $COOR_{10}$; and $R_3$ is ortho or meta to X; provided that $R_3$ is other than $CF_3$;

each $R_9$ and $R_{10}$ is independently $C_{1-6}$alkyl;

$R_{4b}$ is —($C_{1-4}$straight chain alkylene)$R_{15}$; wherein $R_{15}$ is H, $C_{1-7}$alkyl, [di($C_{1-2}$alkyl)amino]($C_{1-6}$alkylene)-, ($C_{1-3}$ alkoxyacyl)($C_{1-6}$alkylene)-, $C_{1-6}$alkoxy, $C_{3-7}$alkenyl or $C_{3-8}$alkynyl;

wherein $R_{4b}$ has no more than 8 carbon atoms;

alternatively, $R_{4b}$ is -(straight chain $C_{1-4}$alkylene)$R_{16}$; wherein $R_{16}$ is $C_{3-6}$cycloalkyl or a 5-6 membered non-aromatic heterocyclyl with between 1 and 2 heteroatoms selected from N, O, and S;

wherein each of the above hydrocarbyl and heterocarbyl moieties may be optionally substituted with between 1 and 3 substituents independently selected from F, Cl, Br, I, amino, methyl, ethyl, hydroxy or methoxy;

comprising

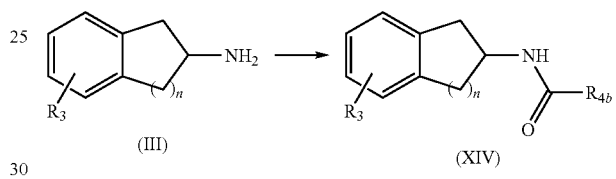

(III)  (XIV)

reacting a suitably substituted compound of formula (III) with a suitably substituted acylating agent capable of attaching an —C(O)—$R_{4b}$ group onto the nitrogen of the compound of formula (III), in the presence of a base, to yield the corresponding compound of formula (XIV);

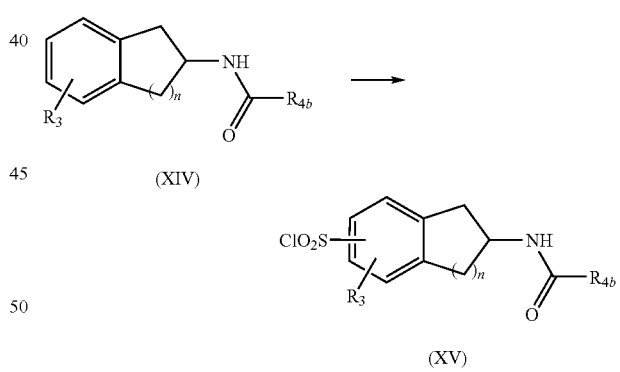

(XIV)

(XV)

reacting the compound of formula (XIV) with $ClSO_3H$, to yield the corresponding compound of formula (XV);

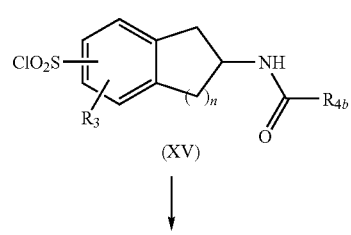

(XV)

-continued

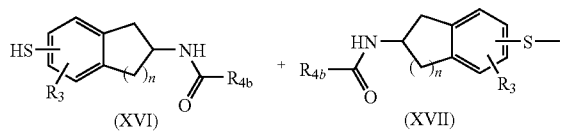

reacting the compound of formula (XV) with a reducing agent capable of reducing the chlorosulfonyl group on the compound of formula (XV), to yield a mixture of the corresponding compound of formula (XVI) and the corresponding compound of formula (XVII);

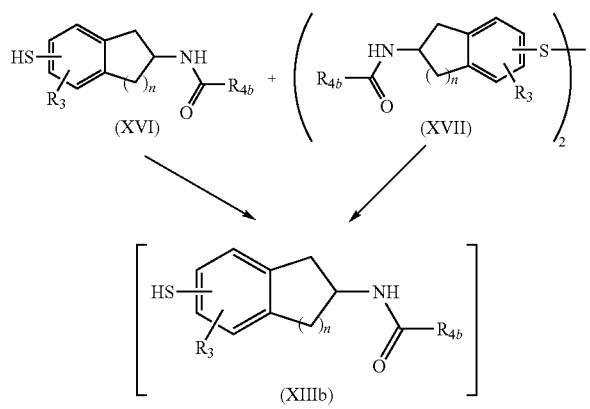

reacting the compound of formula (XVI), isolated or in a mixture with the compound of formula (XVII), with a reducing agent capable of reducing the amide on the compound of formula (XVI), to yield the corresponding compound of formula (XIIIb);

alternatively, reacting the compound of formula (XVII), isolated or in a mixture with the compound of formula (XVI), with a reducing agent capable of reducing the amide and the disulfide on the compound of formula (XVII), to yield the corresponding compound of formula (XIIIb);

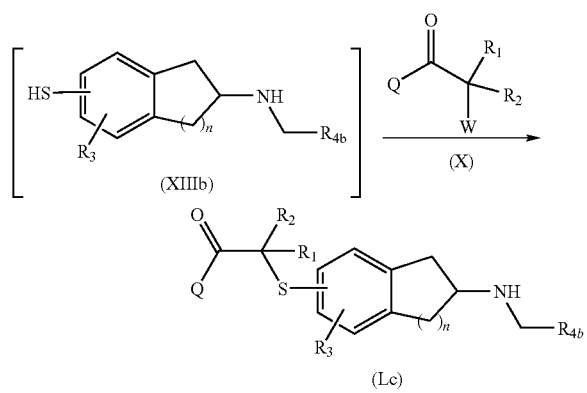

reacting the compound of formula (XIIIb) with a suitably substituted compound of formula (X) wherein W is Br, Cl or I, in the presence of a base, to yield the corresponding compound of formula (Lc).

The present invention is further directed to a process for the preparation of a compound of formula (Lc)

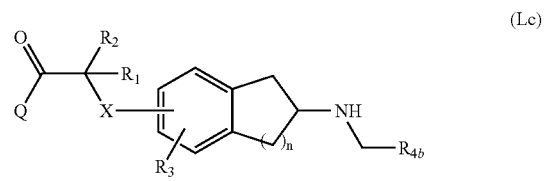

wherein

Q is selected from the group consisting of OH, $OPg^2$, $NH_2$ and $N(Pg^3Pg^4)$; wherein $Pg^2$ is a carboxylic acid protecting group; and wherein $Pg^3$ and $Pg^4$ are each independently selected from hydrogen, $C_{1-8}$alkyl, $C_{3-8}$cycloalkyl or aryl; or $Pg^3$ and $Pg^4$ are taken together with the nitrogen atom to which they are bound to form $C_{3-10}$heteroaryl or $C_{3-10}$non-aromatic heterocyclic;

each of $R_1$ and $R_2$ is independently H, $C_{1-6}$alkyl, $(CH_2)_m NR_aR_b$, $(CH_2)_m OR_8$, $(CH_2)_m NH(CO)R_8$ or $(CH_2)_m CO_2R_8$; wherein each of $R_a$, $R_b$, and $R_8$ is independently H or $C_{1-6}$alkyl; and m is an integer from 1 to 6;

alternatively, $R_1$ and $R_2$ are taken together with the carbon atom to which they are attached to form a $C_{3-7}$cycloalkyl;

n is an integer from 1 to 2;

X is S;

provided that when n is 1, X is bound at the 5 or 6 position; and when n is 2, X is bound at the 6 or 7 position; provided further that when n is 2 and X is bound at the 6 position, then $R^3$ is other than hydrogen and bound at the 7 position;

$R_3$ is H, $C_{1-3}$alkoxy, $C_{1-3}$alkylthio, halo, $C_{1-6}$alkyl, $NR_9R_{10}$, $NHCOR_{10}$, $CONHR_{10}$ or $COOR_{10}$; and $R_3$ is ortho or meta to X; provided that $R_3$ is other than $CF_3$;

each $R_9$ and $R_{10}$ is independently $C_{1-6}$alkyl;

$R_{4b}$ is —$(C_{1-4}$straight chain alkylene$)R_{15}$; wherein $R_{15}$ is H, $C_{1-7}$alkyl, [di($C_{1-2}$alkyl)amino]($C_{1-6}$alkylene)-, ($C_{1-3}$ alkoxyacyl)($C_{1-6}$alkylene)-, $C_{1-6}$alkoxy, $C_{3-7}$alkenyl or $C_{3-8}$alkynyl;

wherein $R_{4b}$ has no more than 8 carbon atoms;

alternatively, $R_{4b}$ is -(straight chain $C_{1-4}$alkylene)$R_{16}$; wherein $R_{16}$ is $C_{3-6}$cycloalkyl or a 5-6 membered non-aromatic heterocyclyl with between 1 and 2 heteroatoms selected from N, O, and S;

wherein each of the above hydrocarbyl and heterocarbyl moieties may be optionally substituted with between 1 and 3 substituents independently selected from F, Cl, Br, I, amino, methyl, ethyl, hydroxy or methoxy;

comprising

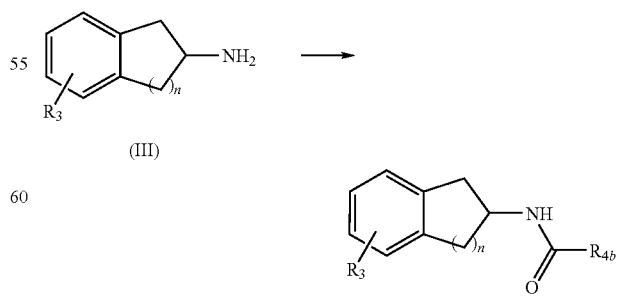

reacting a suitably substituted compound of formula (III) with a suitably substituted acylating agent capable of attaching an —C(O)—R$_{4b}$ group onto the nitrogen of the compound of formula (III), in the presence of a base, to yield the corresponding compound of formula (XIV);

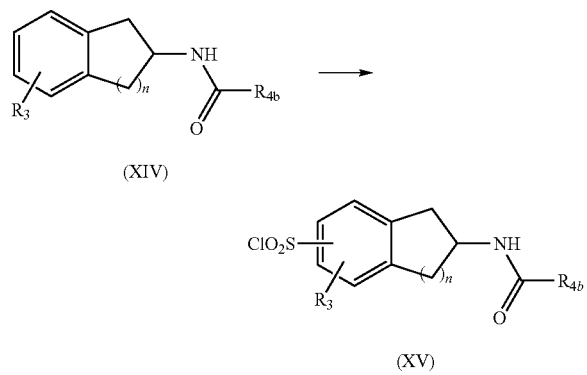

reacting the compound of formula (XIV) with ClSO$_3$H, to yield the corresponding compound of formula (XV);

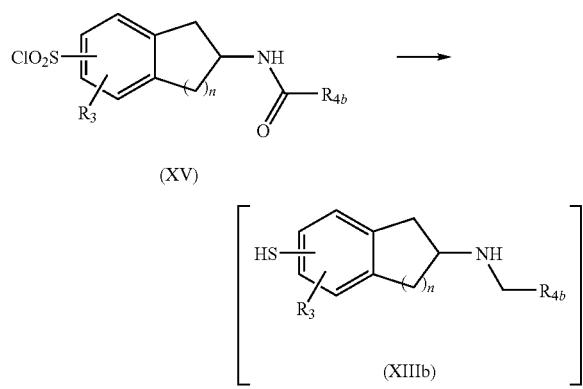

reacting the compound of formula (XV) with a reducing agent capable of reducing the chlorosulfonyl group and the amide group on the compound of formula (XV), to yield the corresponding compound of formula (XIIIb);

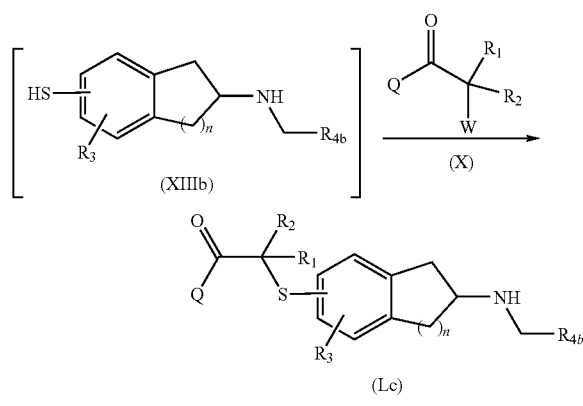

reacting the compound of formula (XIIIb) with a suitably substituted compound of formula (X) wherein W is Br, Cl or I, in the presence of a base, to yield the corresponding compound of formula (Lc).

In an embodiment of the present invention is a process for the preparation of a compound of formula (Ld)

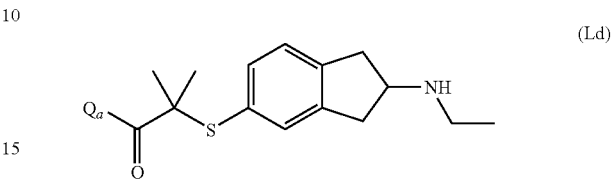

wherein Q$_a$ is OH or OPg$^2$, wherein Pg$^2$ is a carboxylic acid protecting group. In another embodiment of the present invention is a process for the preparation of a compound of formula (Ld) wherein Q$_a$ is OPg$^2$ wherein Pg$^2$ is a carboxylic acid protecting group.

The present invention is further directed to a novel process for the preparation of a compound of formula (I)

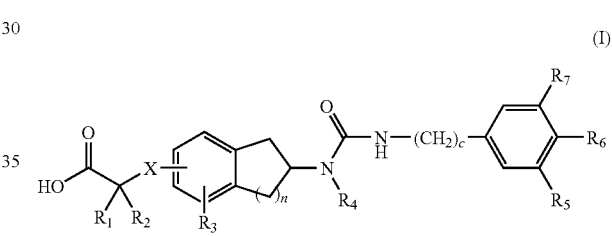

or a pharmaceutically acceptable salt, C$_{1-6}$ ester or C$_{1-6}$ amide thereof,
wherein
each of R$_1$ and R$_2$ is independently H, C$_{1-6}$alkyl, (CH$_2$)$_m$NR$_a$R$_b$, (CH$_2$)$_m$OR$_8$, (CH$_2$)$_m$NH(CO)R$_8$ or (CH$_2$)$_m$CO$_2$R$_8$;
wherein each of R$_a$, R$_b$, and R$_8$ is independently H or C$_{1-6}$alkyl; and m is an integer from 1 to 6;
alternatively, R$_1$ and R$_2$ are taken together with the carbon atom to which they are attached to form a C$_{3-7}$cycloalkyl;
n is an integer from 1 to 2;
X is S;
provided that when n is 1, X is bound at the 5 or 6 position; and when n is 2, X is bound at the 6 or 7 position; provided further that when n is 2 and X is bound at the 6 position, then R$_3$ is other than hydrogen and bound at the 7 position;
R$_3$ is H, C$_{1-3}$alkoxy, C$_{1-3}$alkylthio, halo, C$_{1-6}$alkyl, NR$_9$R$_{10}$, NHCOR$_{10}$, CONHR$_{10}$ or COOR$_{10}$; and R$^3$ is ortho or meta to X; provided that R$_3$ is other than CF$_3$;
each R$_9$ and R$_{10}$ is independently C$_{1-6}$alkyl;
R$_4$ is H or —(C$_{1-5}$straight chain alkylene)R$_{15}$; wherein R$_{15}$ is H, C$_{1-7}$alkyl, [di(C$_{1-2}$alkyl)amino](C$_{1-6}$alkylene)-, (C$_{1-3}$alkoxyacyl)(C$_{1-6}$alkylene)-, C$_{1-6}$alkoxy, C$_{3-7}$alkenyl or C$_{3-8}$alkynyl;
wherein R$_4$ has no more than 9 carbon atoms;

alternatively, $R_4$ is -(straight chain $C_{1-5}$alkylene)$R_{16}$; wherein $R_{16}$ is $C_{3-6}$cycloalkyl or a 5-6 membered non-aromatic heterocyclyl with between 1 and 2 heteroatoms selected from N, O, and S;

c is an integer from 0 to 1;

each of $R_5$ and $R_7$ is independently selected from H, $C_{1-6}$alkyl, halo, cyano, nitro, $COR_{11}$, $COOR_{11}$, $C_{1-4}$alkoxy, $C_{1-4}$alkylthio, hydroxy, phenyl, $NR_{11}R_{12}$ or a 5-6 membered heterocyclyl with between 1 and 2 heteroatoms selected from N, O, and S;

$R_6$ is selected from $C_{1-6}$alkyl, halo, cyano, nitro, $COR_{13}$, $COOR_{13}$, $C_{1-4}$alkoxy, $C_{1-4}$alkylthio, hydroxy, phenyl, $NR_{13}R_{14}$ or a 5-6 membered heterocyclyl with between 1 and 2 heteroatoms selected from N, O, and S;

alternatively, $R_5$ and $R_6$ or $R_6$ and $R_7$ may be taken together to be a bivalent moiety, saturated or unsaturated, selected from $C_{3-4}$alkylene (for example, —(CH$_2$)$_3$— or —(CH$_2$)$_4$—), $C_{3-4}$alkenylene (for example, —CH═CH—CH$_2$— or —CH═CH—CH═CH—) or (CH$_{1-2}$)$_p$N(CH$_{1-2}$)$_q$;

p is an integer from 0 to 2 and q is an integer from 1 to 3; wherein the sum (p+q) is at least 2;

each $R_{11}$, $R_{12}$, $R_{13}$ and $R_{14}$ is independently H or $C_{1-6}$alkyl;

wherein each of the above hydrocarbyl and heterocarbyl moieties may be optionally substituted with between 1 and 3 substituents independently selected from F, Cl, Br, I, amino, methyl, ethyl, hydroxy or methoxy;

comprising

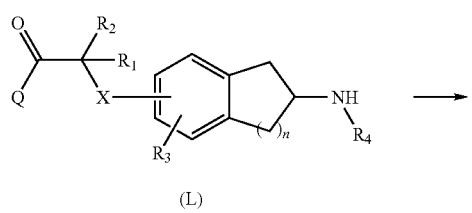

(L)

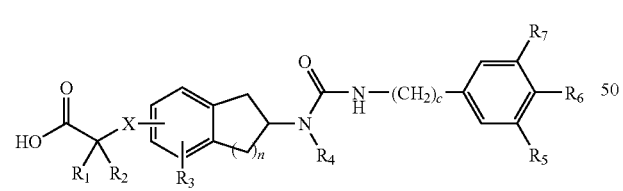

(I)

reacting a compound of formula (L), wherein Q is selected from the group consisting of OH, OPg$^2$, NH$_2$ and N(Pg$^3$Pg$^4$); wherein Pg$^2$ is a carboxylic acid protecting group; and wherein Pg$^3$ and Pg$^4$ are each independently selected from hydrogen, $C_{1-8}$alkyl, $C_{3-8}$cycloalkyl or aryl; or Pg$^3$ and Pg$^4$ are taken together with the nitrogen atom to which they are bound to form $C_{3-10}$heteroaryl or $C_{3-10}$non-aromatic heterocyclic; to yield the corresponding compound of formula (I).

In an embodiment of the present invention is a process for the preparation of a compound of formula (II)

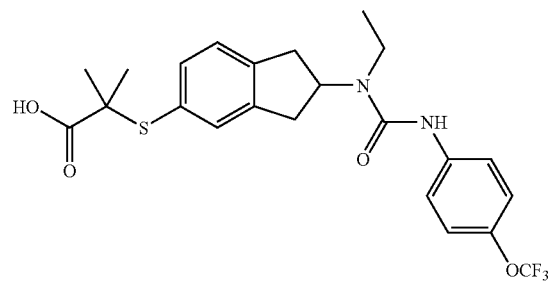

(II)

also known as 2-[[2-[ethyl[[[4-(trifluoromethoxy)phenyl]amino]carbonyl]amino]-2,3-dihydro-1H-inden-5-yl]thio]-2-methyl-propanoic acid or 2-{2-[1-ethyl-3-(4-trifluoromethoxy-phenyl)-ureido]-indan-5-ylsulfanyl}-2-methyl-propionic acid.

In another embodiment of the present invention is a process for the preparation of a compound of formula (IIa)

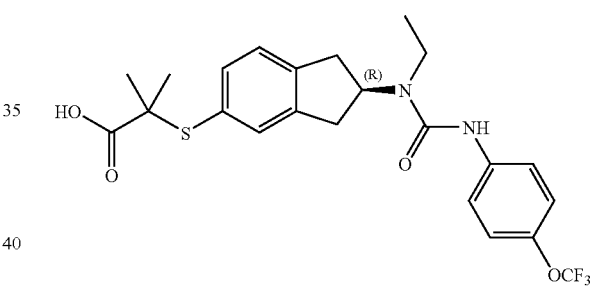

(IIa)

also known as 2-[[(2R)-2-[ethyl[[[4-(trifluoromethoxy)phenyl]amino]carbonyl]amino]-2,3-dihydro-1H-inden-5-yl]thio]-2-methyl-propanoic acid or 2-{(2R)-[1-ethyl-3-(4-trifluoromethoxy-phenyl)-ureido]-indan-5-ylsulfanyl}-2-methyl-propionic acid.

The present invention is further directed to a process for the preparation of the compound of formula (Le)

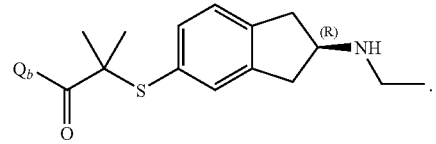

(Le)

wherein $Q_b$ is selected from the group consisting of $C_{1-6}$alkoxy, wherein the $C_{1-6}$alkoxy is not substituted with amino; comprising

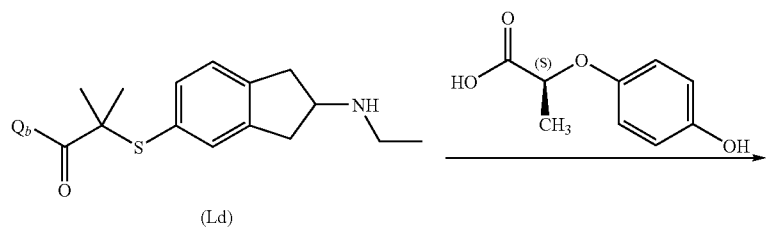

(Ld)

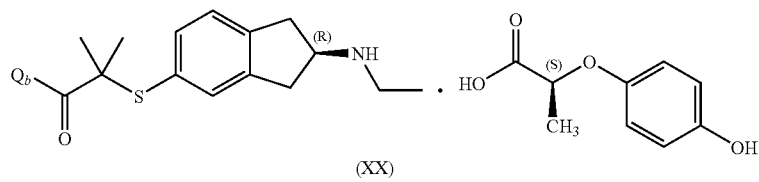

(XX)

(a) reacting a compound of formula (Ld) with (S)-2-(4-hydroxyphenoxy)propionic acid, in an alcohol; or in acetone, at a temperature in the range of from about 35° C. to about 0° C.; to yield the corresponding (R,S) diastereomeric salt, the compound of formula (XX);

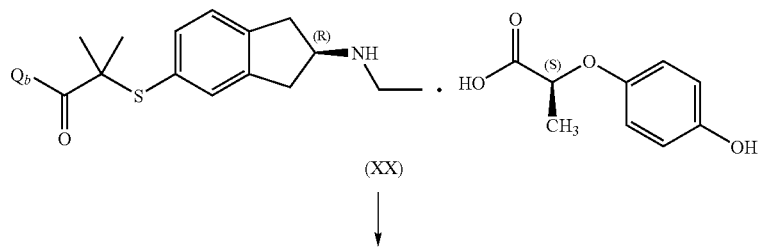

(XX)

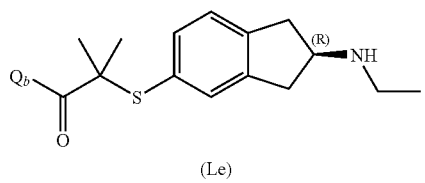

(Le)

(b) reacting the (R,S) diastereomeric salt, the compound of formula (XX), with an inorganic base, to yield the corresponding compound of formula (Le).

The present invention is further directed to a process for the preparation of the compound of formula (Le)

(Le)

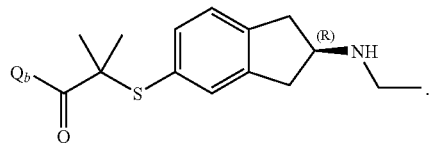

wherein $Q_b$ is selected from the group consisting of $C_{1-6}$alkoxy, wherein the $C_{1-6}$alkoxy is not substituted with amino; comprising

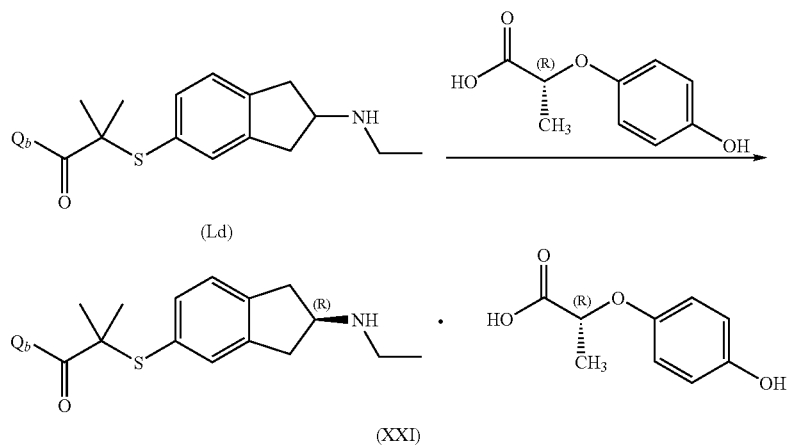

(a) reacting a compound of formula (Ld) with (R)-2-(4-hydroxyphenoxy)propionic acid, in acetone, at a temperature greater than about 35° C., preferably at a temperature greater than about 45° C.; or in THF at about room temperature, to yield the corresponding (R,R) diastereomeric salt, the compound of formula (XXI).

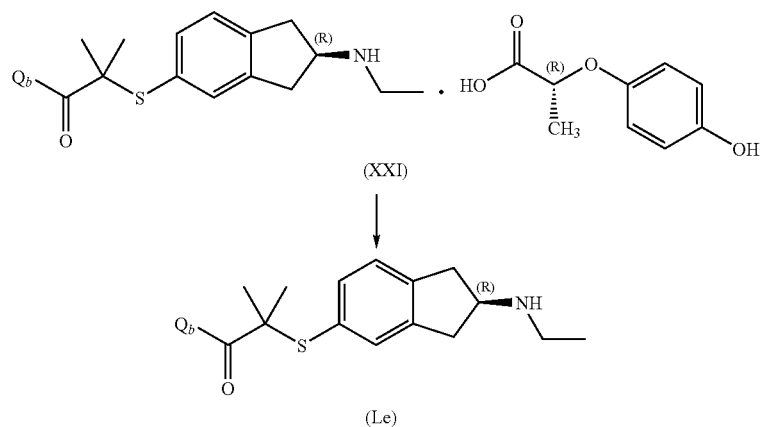

(b) reacting the (R,R) diastereomeric salt, the compound of formula (XXI) with an inorganic base, to yield the corresponding compound of formula (Le).

The present invention is further directed to a process for the preparation of the compound of formula (Lf)

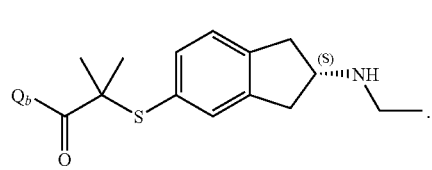

wherein $Q_b$ is selected from the group consisting of $C_{1-6}$alkoxy, wherein the $C_{1-6}$alkoxy is not substituted with amino; comprising

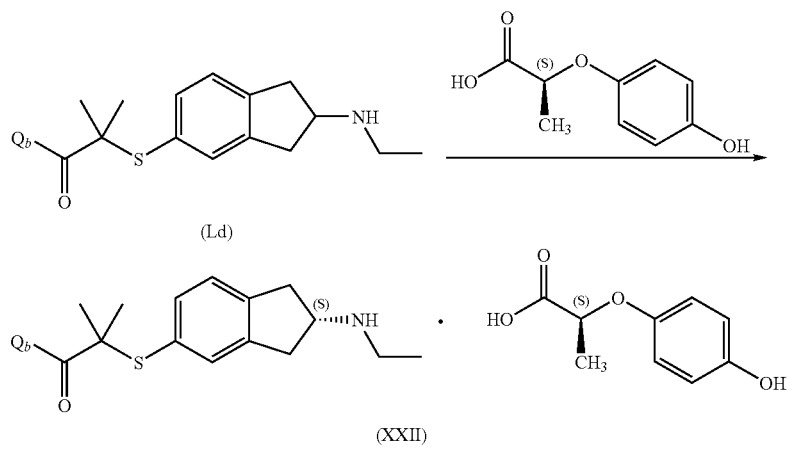

(a) reacting a compound of formula (Ld) with (S)-2-(4-hydroxyphenoxy)propionic acid, in acetone, at a temperature greater than about 35° C., preferably at a temperature greater than about 45° C.; or in THF at about room temperature; to yield the corresponding (S,S) diastereomeric salt, the compound of formula (XXII).

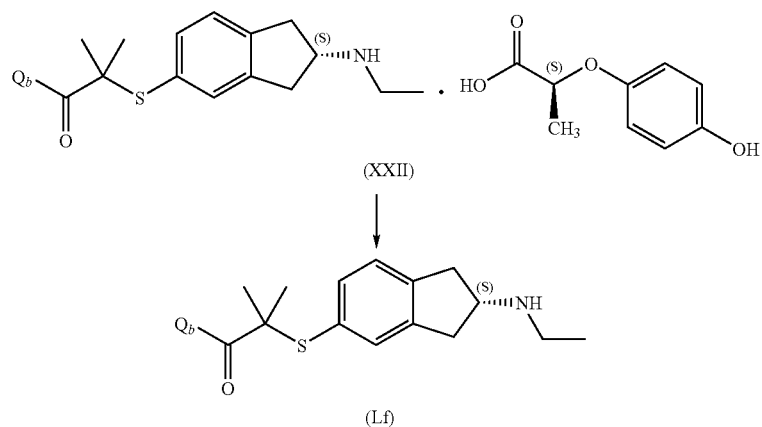

(b) reacting the (S,S) diastereomeric salt, the compound of formula (XXI) with an inorganic base, to yield the corresponding compound of formula (Lf).

The present invention is further directed to a process for the preparation of the compound of formula (Lf)

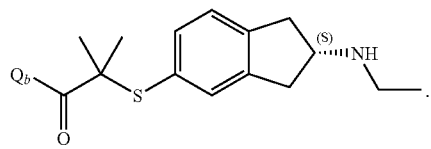

wherein $Q_b$ is selected from the group consisting of $C_{1-6}$alkoxy, wherein the $C_{1-6}$alkoxy is not substituted with amino; comprising

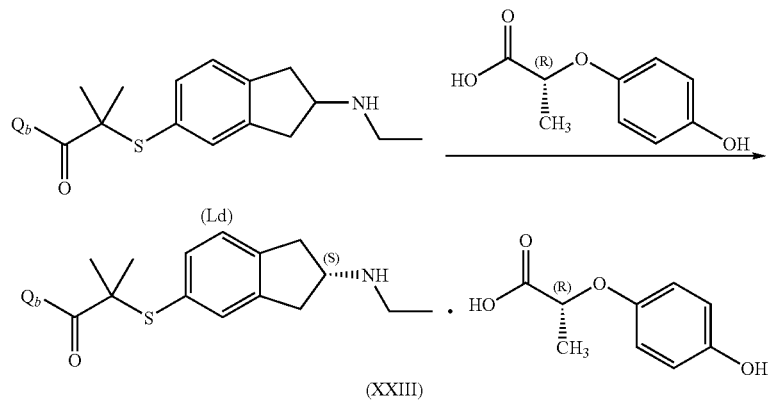

(a) reacting a compound of formula (Ld) with (R)-2-(4-hydroxyphenoxy)propionic acid, in an alcohol; or in acetone, at a temperature in the range of from about 35° C. to about 0° C.; to yield the corresponding (S,R) diastereomeric salt, the compound of formula (XXIII);

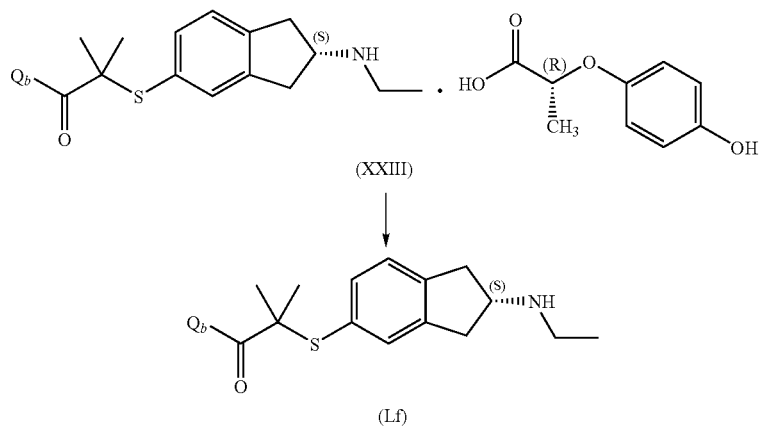

(b) reacting the (S,R) diastereomeric salt, the compound of formula (XXIII) with an inorganic base, to yield the corresponding compound of formula (Lf).

The present invention is further directed to a novel crystalline salt of the compound of formula (IIa), more specifically, an N,N'-dibenzylethylenediamine (benzathine) salt of the compound of formula (IIa). The present invention is further directed to an N,N'-dibenzylethylenediamine salt of the compound of formula (IIa) wherein the ratio of the compound of formula (IIa) to the N,N'-dibenzylethylenediamine is 1:1. The present invention is further directed to a process for the preparation of the benzathine salt of the compound of formula (IIa).

The present invention is further directed to a compound prepared according to any of the processes described herein.

Illustrative of the invention is a pharmaceutical composition comprising a pharmaceutically acceptable carrier and a compound prepared according to any of the processes described herein. An illustration of the invention is a pharmaceutical composition made by mixing a compound prepared according to any of the processes described herein and a pharmaceutically acceptable carrier. Illustrating the invention is a process for making a pharmaceutical composition comprising mixing a compound prepared according to any of the processes described herein and a pharmaceutically acceptable carrier.

In one embodiment, the pharmaceutical composition comprises the compound:

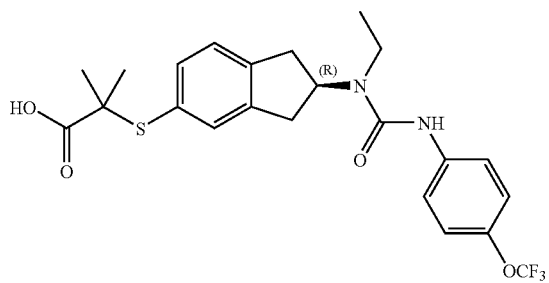

or a pharmaceutically acceptable salt, $C_{1-6}$ ester or $C_{1-6}$ amide thereof.

In another embodiment, the pharmaceutical composition comprises the compound:

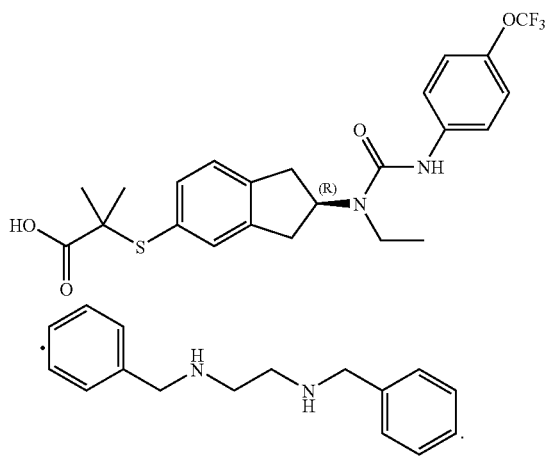

Exemplifying the present invention are methods of treating a PPAR alpha-mediated disease in a subject in need thereof comprising administering to the subject a therapeutically effective amount of a compound prepared according to any of the processes described herein or a pharmaceutical composition as described above. Further exemplifying the present invention are methods of elevating serum levels of high density lipoproteins (HDL), improving levels of intermediate density lipoproteins (IDL), lowering serum levels of triglycerides, low density lipoproteins (LDL), atherogenic molecules, and/or free fatty acids (FFA), treating hypertriglyceridemia, raising levels of HDL, lowering levels of LDL, and/or lowering total cholesterol, in a subject in need thereof comprising administering to the subject a therapeutically effective amount of a compound prepared according to any of the processes described herein or a pharmaceutical composition as described above.

Further exemplifying the invention are methods for treating dyslipidemia, cardiovascular disorders, impaired glucose tolerance, hyperinsulinemia, hyperglycemia, insulin resistance, early, intermediate or late Type II diabetes (NIDDM), complications thereof, or Syndrome X, in a subject in need thereof comprising administering to the subject a therapeutically effective amount of a compound prepared according to any of the processes described herein or a pharmaceutical composition as described above.

Further exemplifying the invention are methods for the treatment, prevention, or for inhibiting the progression of one or more of the following conditions or diseases: phase I hyperlipidemia; pre-clinical hyperlipidemia; phase II hyperlipidemia; hypertension; CAD (coronary artery disease); coronary heart disease; hypertriglyceridemia; lowering serum levels of low-density lipoproteins (LDL), IDL, and/or small-density LDL and other atherogenic molecules, or molecules that cause atherosclerotic complications, thereby reducing cardiovascular complications; elevating serum levels of high-density lipoproteins (HDL); lowering serum levels of triglycerides, LDL, and/or free fatty acids; and/or lowering FPG/HbA1c.

Another example of the invention is the use of a compound prepared according to any of the processes described herein in the preparation of a medicament for treating (a) dyslipidemia, (b) cardiovascular disorders, (c) impaired glucose tolerance, (d) hyperinsulinemia, (e) hyperglycemia, (f) insulin resistance, (g) early Type II diabetes (NIDDM), (h) intermediate Type II diabetes (NIDDM), (i) late Type II diabetes (NIDDM), (j) complications of Type II diabetes or (k) Syndrome X, in a subject in need thereof.

DETAILED DESCRIPTION OF THE INVENTION

"Alkyl" includes optionally substituted straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. As used herein, alkyl also includes cycloalkyl, such as cyclopropyl, cyclobutyl, cyclopentyl, and cyclohexyl.

"Alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. As used herein, alkenyl also includes cycloalkenyl. Cis and trans or (E) and (Z) forms are included within the invention.

"Alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes an optionally substituted straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

"Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

"Aryl" includes phenyl, naphthyl, biphenylyl, tetrahydronaphthyl, indenyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridge, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on.

"Heterocyclyl" includes optionally substituted aromatic and nonaromatic rings having carbon atoms and at least one heteroatom (O, S, N) or heteroatom moiety ($SO_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 5 and 7 ring atoms, or between 5 and 6 ring atoms; there may be between 1 and 5 heteroatoms or heteroatom moieties in the ring, and preferably between 1 and 3, or between 1 and 2. A heterocyclyl may be saturated, unsaturated, aromatic (e.g., heteroaryl), nonaromatic, or fused.

Heterocyclyl also includes fused, e.g., bicyclic, rings, such as those optionally condensed with an optionally substituted carbocyclic or heterocyclic five- or six-membered aromatic ring. For example, "heteroaryl" includes an optionally substituted six-membered heteroaromatic ring containing 1, 2 or 3 nitrogen atoms condensed with an optionally substituted five- or six-membered carbocyclic or heterocyclic aromatic ring. Said heterocyclic five- or six-membered aromatic ring condensed with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

Examples of heterocyclyls include thiazoylyl, furyl, thienyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, thienyl, and more preferably, piperidyl or morpholinyl.

Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl.

"Acyl" refers to a carbonyl moiety attached to either a hydrogen atom (i.e., a formyl group) or to an optionally substituted alkyl or alkenyl chain, or heterocyclyl.

"Halo" or "halogen" includes fluoro, chloro, bromo, and iodo, and preferably fluoro or chloro as a substituent on an alkyl group, with one or more halo atoms, such as trifluoromethyl, trifluoromethoxy, trifluoromethylthio, difluoromethoxy, or fluoromethylthio.

"Alkanediyl" or "alkylene" represents straight or branched chain optionally substituted bivalent alkane radicals such as, for example, methylene, ethylene, propylene, butylene, pentylene or hexylene.

"Alkenediyl" represents, analogous to the above, straight or branched chain optionally substituted bivalent alkene radicals such as, for example, propenylene, butenylene, pentenylene or hexenylene. In such radicals, the carbon atom linking a nitrogen preferably should be saturated.

"Aroyl" refers to a carbonyl moiety attached to an optionally substituted aryl or heteroaryl group, wherein aryl and heteroaryl have the definitions provided above. In particular, benzoyl is phenylcarbonyl.

As defined herein, two radicals, together with the atom(s) to which they are attached may form an optionally substituted 4- to 7-, 5- to 7-, or a 5- to 6-membered ring carbocyclic or heterocyclic ring, which ring may be saturated, unsaturated or aromatic. Said rings may be as defined above in the Summary of the Invention section.

"Enantiomer excess" or "ee", usually expressed as a percentage, describes the excess of one enantiomer over the other. The percentage enantiomer excess, ee=100(Xr–Xs)/(Xr+Xs), where Xr>Xs. Alternatively, ee=100(2X−1), where X is the mole fraction of the dominant enantiomer in the mixture. Please note that Xr and Xs represent the mole fraction of (R)-enantiomer and (S)-enantiomer respectively in the mixture.

"Pharmaceutically acceptable salts, esters, and amides" include carboxylate salts, amino acid addition salts, esters, and amides which are within a reasonable benefit/risk ratio, pharmacologically effective and suitable for contact with the tissues of patients without undue toxicity, irritation, or allergic response. These salts, esters, and amides may be, for example, $C_{1-8}$alkyl, $C_{3-8}$cycloalkyl, aryl, $C_{2-10}$heteroaryl, or $C_{2-10}$non-aromatic heterocyclic salts, esters, and amides. Salts, free acids, and esters are more preferable than amides on the terminal carboxylate/carboxylic acid group on the left of formula (I). Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1-19 which is incorporated herein by reference. Representative pharmaceutically acceptable amides of the invention include those derived from ammonia, primary $C_{1-6}$alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines. Representative pharmaceutically acceptable esters of the invention include $C_{1-7}$ alkyl, $C_{5-7}$cycloalkyl, phenyl, and phenyl($C_{1-6}$) alkyl esters. Preferred esters include methyl and ethyl esters.

As used herein, all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context. The context will indicate that the substituent is an alkylene or hydrocarbon radical with at least two hydrogen atoms removed (bivalent) or more hydrogen atoms removed (multivalent).

Radicals or structure fragments as defined herein are understood to include substituted radicals or structure fragments. Hydrocarbyls include monovalent radicals containing carbon and hydrogen such as alkyl, alkenyl, alkynyl, cycloalkyl, and cycloalkenyl (whether aromatic or unsaturated), as well as corresponding bivalent (or multi-valent) radicals such as alkylene, alkenylene, phenylene, and so on. Heterocarbyls include monovalent and bivalent (or multi-valent) radicals containing carbon, optionally hydrogen, and at least one heteroatom. Examples of monovalent heterocarbyls include acyl, acyloxy, alkoxyacyl, heterocyclyl, heteroaryl, aroyl, benzoyl, dialkylamino, hydroxyalkyl, and so on. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl) or different (chlorofluoro-, chlorobenzyl- or aminomethyl-substituted). Examples of substituted alkyl include haloalkyl (such as fluoromethyl, chloromethyl, difluoromethyl, perchloromethyl, 2-bromoethyl, trifluoromethyl, and 3-iodocyclopentyl), hydroxyalkyl (such as hydroxymethyl, hydroxyethyl, 2-hydroxypropyl), aminoalkyl (such as aminomethyl, 2-aminoethyl, 3-aminopropyl, and 2-aminopropyl), alkylalkyl, and so on. A di($C_{1-6}$alkyl)amino group includes independently selected alkyl groups, to form, for example, methylpropylamino and isopropylmethylamino, in addition dialkylamino groups having two of the same alkyl group such as dimethylamino or diethylamino.

Only stable compounds are intended. For example, where there is an $NR_{11}R_{12}$ group, and R can be an alkenyl group, the double bond is at least one carbon removed from the nitrogen to avoid enamine formation. Similarly, where —$(CH_2)_p$—N—$(CH_2)_q$— can be unsaturated, the appropriate hydrogen atom(s) is(are) included or omitted, as shown in —$(CH_2)$—N═(CH)—$(CH_2)$— or —$(CH_2)$—NH—(CH)═(CH)—.

Unless otherwise noted, when naming substituents such as X and $R_3$, the following numbering of the indane and tetralin, respectively, will be applied.

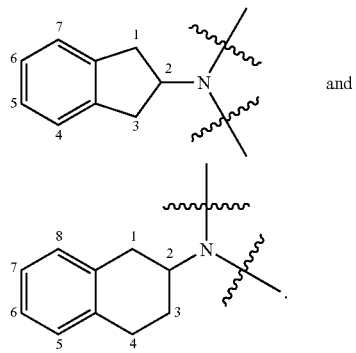

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "carboxylic acid protecting group" shall mean a group which may be attached to —C(O)O— portion of the carboxylic acid to protect said carboxylic acid from participating in a reaction and which may be readily removed following the reaction. Suitable carboxylic acid protecting groups include, but are not limited $C_{1-7}$alkyl, $C_{5-7}$cycloalkyl, phenyl, phenyl$C_{1-6}$alkyl, and the like. Other suitable carboxylic acid protecting groups may be found in texts such as T. W. Greene & P. G. M. Wuts, *Protective Groups in Organic Synthesis*, John Wiley & Sons, 1991.

In the process for the preparation of the compounds of formula (I), application of the present invention to a mixture of enantiomers of the compound of formula (L), substantially free of the S enantiomer, will result in the production of a mixture of enantiomers of formula (I), substantially free of the S enantiomer. Similarly, in the process for the preparation of the compounds of formula (I), application of the present invention to a mixture of enantiomers of formula (L), substantially free of the R enantiomer, will result in the production of a mixture of enantiomers of formula (I), substantially free of the R enantiomer. Preferably, the enantiomeric excess of the desired enantiomer of formula (I) is at least about 90% ee, more preferably, at least about 96% ee, most preferably, about 99% ee.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

With reference to substituents, the term "independently" means that when more than one of such substituents is possible, such substituents may be the same or different from each other.

When a particular group is "substituted" (e.g., phenyl, aryl, aralkyl, heteroaryl), that group may have one or more substituents, preferably from one to three substituents, more preferably from one to two substituents, independently selected from the list of substituents.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly the Schemes and Examples, are as follows

| | |
|---|---|
| Ac = | Acetyl (i.e. —C(O)—CH$_3$) |
| ACN or MeCN = | Acetonitrile |
| Alloc = | CH$_2$=CHCH$_2$—O—C(O)— |
| DCE = | Dichloroethane |
| DCM = | Dichloromethane |
| DIPEA or DIEA = | Diisopropylethylamine |
| DMA = | Dimethylacetamide |
| DMF = | N,N-Dimethylformamide |
| DMSO = | Dimethyl sulfoxide |
| % ee = | Percent Enantiomeric Excess |
| Et$_3$N or TEA = | Triethylamine |
| EtOAc = | Ethyl acetate |
| EtOH = | Ethanol |
| FTIR = | Fourier Transform Infra-Red |
| HPLC = | High Pressure Liquid Chromatography |
| iPrOAc = | Isopropyl acetate |
| KF = | Karl-Fisher (% water measurement) |
| LAH = | Lithium Aluminum Hydride |
| LDA = | Lithium Diisopropylamide |
| LHMDS = | Lithium bis(trimethylsilyl)amide |
| MeOH = | Methanol |
| mp = | Melting Point |
| MS = | Mass Spectroscopy |
| MTBE = | Methyl-t-butyl ether |
| MTr = | 2,3,6-trimethyl-4-methoxy-phenyl-sulfonyl |
| NMR = | Nuclear Magnetic Resonance |
| Pd(PPh$_3$)$_4$ = | Palladium (0) Tetrakis(triphenylphosphine) |
| TFA = | Trifluoroacetic Acid |
| THF = | Tetrahydrofuran |

In an embodiment of the present invention, in the compound of formula (I), (a) one of R$_1$ and R$_2$ is methyl or ethyl; (b) each of R$_1$ and R$_2$ is methyl; (c) R$_1$ and R$_2$ taken together are cyclobutyl or cyclopentyl; (d) R$_3$ is H; (e) R$_4$ is H or C$_{2-7}$alkyl; (e) R$_4$ is H or C$_{2-5}$alkyl; (f) R$_4$ is ethyl; (g) R$_4$ is H; (h) n is 1; (i) n is 2; (j) at least one of R$_5$ and R$_7$ is H; (k) R$_6$ is C$_{1-4}$alkyl, halomethoxy, or halothiomethoxy (i.e —S-(halomethyl)); (l) R$_6$ is t-butyl, isopropyl, trifluoromethyl, trifluoromethoxy, trifluorothiomethoxy (i.e. —S—CF$_3$), difluoromethoxy, or dimethylamino; (m) R$_3$ is H, R$_4$ is C$_{2-7}$alkyl; (n) R$_4$ is C$_{2-5}$alkyl; (o) R$_6$ is cyclopropylmethyl, isopropyl, isobutyl, methylethylamino, or diethylamino; (p) the (S) enantiomer at the C-2 position on the indane or tetralin; (q) the (R) entantiomer at the C-2 position on the indane or tetralin; (r) where R$_{15}$ is C$_{1-7}$ alkyl, [di(C$_{1-2}$ alkyl)amino](C$_{1-6}$alkylene), (C$_{1-3}$alkoxyacyl)(C$_{1-6}$alkylene), C$_{1-6}$alkoxy, C$_{3-7}$alkenyl, or C$_{3-8}$alkynyl; (s) R$_6$ is trifluoromethylthio or trifluoromethoxy; or (t) any combination of the above.

In another embodiment of the present invention, the compound of formula (I) selected from the group consisting of 2-{6-[1-Ethyl-3-(4-trifluoromethoxyphenyl)ureido]-3-methoxy-5,6,7,8-tetrahydronaphthalen-2-ylsulfanyl}-2-methylpropionic acid; 2-{6-[1-Ethyl-3-(4-trifluoromethoxyphenyl)ureido]-3-fluoro-5,6,7,8-tetrahydronaphthalen-2-ylsulfanyl}-2-methylpropionic acid; 2-{6-[1-Ethyl-3-(4-trifluoromethoxyphenyl)ureido]-3-chloro-5,6,7,8-tetrahydronaphthalen-2-ylsulfanyl}-2-methylpropionic acid; 2-{6-[1-Ethyl-3-(4-trifluoromethoxyphenyl)ureido]-3-bromo-5,6,7,8-tetrahydronaphthalen-2-ylsulfanyl}-2-methylpropionic acid; 2-{6-[1-Ethyl-3-(4-trifluoromethoxyphenyl)ureido]-3-methyl-5,6,7,8-tetrahydronaphthalen-2-ylsulfanyl}-2-methylpropionic acid; 2-{6-[1-Ethyl-3-(4-trifluoromethoxyphenyl)ureido]-3-trifluoromethoxy-5,6,7,8-tetrahydronaphthalen-2-ylsulfanyl}-2-methylpropionic acid; 2-{6-[1-Ethyl-3-(4-hydroxyphenyl)ureido]-5,6,7,8-tetrahydronaphthalen-2-ylsulfanyl}-2-methylpropionic acid; 2-{6-[(4-Aminophenyl)-1-ethyl-ureido]-5,6,7,8-tetrahydronaphthalen-2-ylsulfanyl}-2-methylpropionic acid and 2-{6-[1-Ethyl-3-(4-trifluoromethoxyphenyl)ureido]-4-trifluoromethyl-5,6,7,8-tetrahydronaphthalen-2-ylsulfanyl}-2-methylpropionic acid.

In another embodiment of the present invention the compound of formula (I) selected from the group consisting of 2-{6-[1-Ethyl-3-(4-trifluoromethoxyphenyl)ureido]-5,6,7,8-tetrahydronaphthalen-2-ylsulfanyl}-2-methylpropionic acid; 2-{6-[3-(4-trifluoromethoxyphenyl)ureido]-5,6,7,8-tetrahydronaphthalen-2-ylsulfanyl}-2-methylpropionic acid; 2-{2-[1-Ethyl-3-(4-trifluoromethoxyphenyl)ureido]indan-5-ylsulfanyl}-2-methylpropionic acid; 2-{2-[1-Ethyl-3-(4-trifluoromethylsulfanylphenyl)ureido]indan-5-ylsulfanyl}-2-methylpropionic acid; and 2-Methyl-2-{2-[1-propyl-3-(4-trifluoromethoxyphenyl)ureido]indan-5-ylsulfanyl}propionic acid.

In an embodiment of the present invention c is 0. In another embodiment of the present invention n is 1 and X is bound at the 5-position. In yet another embodiment of the present invention n is 2 and X is bound at the 6- or 7-position, preferably at the 6-position.

In an embodiment of the present invention, wherein n is 1 and R$_3$ is hydrogen or is other than hydrogen and is bound at the 4-, 6- or 7-position, then the —X—C(R$_1$R$_2$)—C(O)-Q group is bound at the 5-position. In another embodiment of the present invention, wherein n is 1 and R$_3$ is hydrogen or is other than hydrogen and is bound at the 4-, 6- or 7-position, then the —X—C(R$_1$R$_2$)—C(O)—OH group is bound at the 5-position.

In an embodiment of the present invention, wherein n is 1 and R$_3$ is other than hydrogen and is bound at the 5-position, then the —X—C(R$_1$R$_2$)—C(O)-Q group is bound at the 6-position. In another embodiment of the present invention, wherein n is 1 and R$_3$ is other than hydrogen and is bound at the 5-position, then the —X—C(R$_1$R$_2$)—C(O)—OH group is bound at the 6-position.

In an embodiment of the present invention Q is OPg$^2$ or N(Pg$^3$Pg$^4$), wherein Pg$^2$ is a carboxylic acid protecting group as readily understood by one skilled in the art, including, but not limited to, C$_{1-7}$alkyl, C$_{5-7}$cycloalkyl, phenyl, phenylC$_{1-6}$alkyl, and the like; and Pg$^3$ and Pg$^4$ are each independently selected from hydrogen, C$_{1-8}$alkyl, C$_{3-8}$cycloalkyl or aryl; alternatively Pg$^3$ and Pg$^4$ are taken together with the nitrogen atom to which they are bound to form C$_{3-10}$heteroaryl or C$_{3-10}$non-aromatic heterocyclic, preferably a 5- or 6-membered heterocyclic or heteroaromatic ring moiety containing at least one nitrogen atom and optionally between 1 and 2 additional heteroatoms. In another embodiment of the present invention Q is OPg$^2$, wherein Pg$^2$ is a carboxylic acid protecting group.

In an embodiment of the present invention Q is selected from the group consisting of hydroxy, unsubstituted C$_{1-6}$alkoxy, amino, unsubstituted C$_{1-4}$alkylamino and di(unsubstituted C$_{1-4}$alkyl)amino. In another embodiment of the present invention Q is selected from the group consisting of hydroxy, methoxy, ethoxy, ispropyloxy, n-butyloxy, t-butoxy, amino, methylamino and dimethylamino. In yet another embodiment of the present invention Q is C$_{1-6}$alkoxy, wherein the C$_{1-6}$alkoxy is not substituted with amino. In yet another embodiment of the present invention, Q is selected from the group consisting of methoxy, ethoxy and t-butoxy.

The present invention is directed to a process for the preparation of compounds of formula (L)

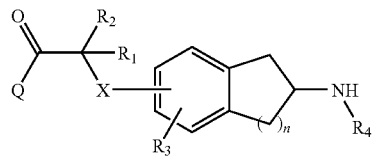

wherein Q, X, $R_1$, $R_2$, $R_3$, n and $R_4$ are as herein defined. The compounds of formula (L) are useful as intermediates in the preparation of compounds of formula (I).

Compounds of formula (L) may be prepared according to the process outlined in Scheme 1.

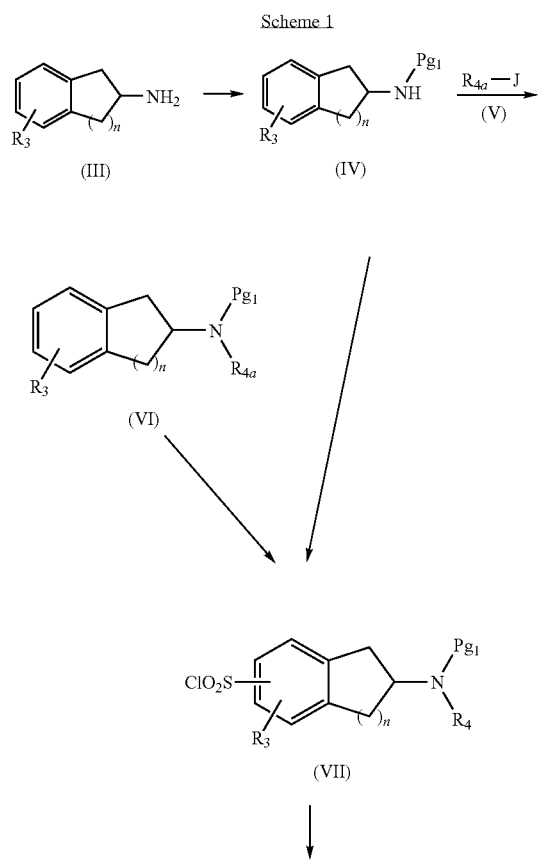

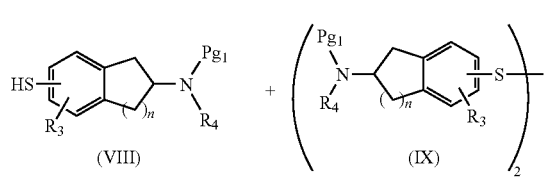

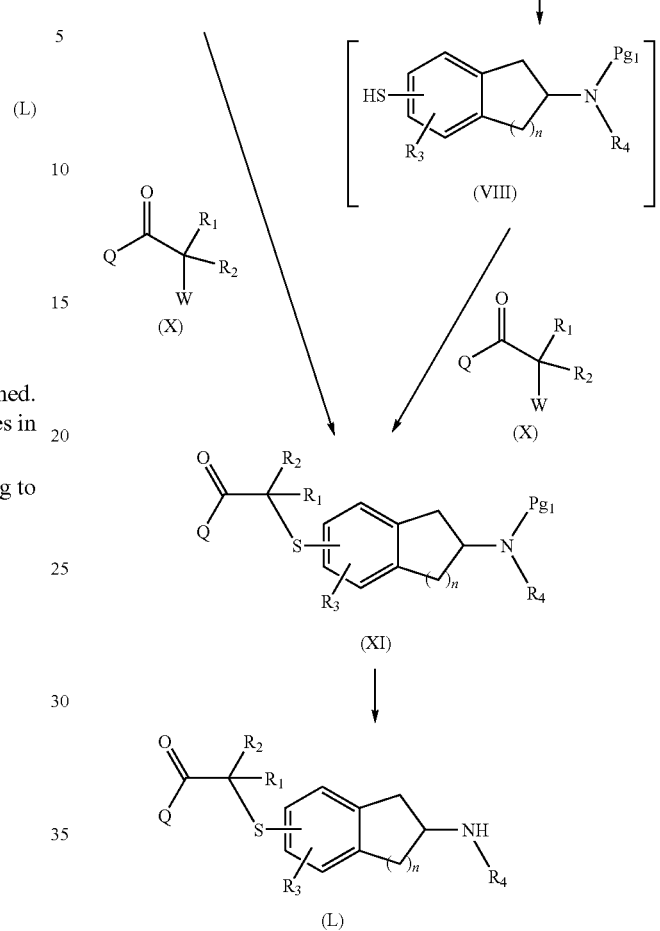

Accordingly, a suitably substituted compound of formula (III), a known compound or compound prepared by known methods, is reacted (for example, protected) according to known methods, to yield the corresponding compound of formula (IV), wherein $Pg_1$ is a nitrogen protecting group which is inert to $ClSO_3H$, such as, Alloc ($CH_2$=$CHCH_2$—O—C(O)—), acetyl ($CH_3$—C(O)—), ($C_{1-4}$alkyl)-C(O)—, and the like. For example, the compound of formula (III) is reacted with a suitably selected protecting reagent such as Alloc-Cl ($CH_2$=$CHCH_2$—O—C(O)—Cl), $Alloc_2O$ ($CH_2$=$CHCH_2$—OC(O)—O—C(O)O—$CH_2$CH=$CH_2$), AcCl ($CH_3$—C(O)—Cl), $Ac_2O$ ($CH_3$—C(O)—O—C(O)—$CH_3$), and the like. Wherein the compound of formula (III) is reacted with a Alloc-Cl, or $Alloc_2O$, the corresponding protecting group $Pg_1$ is Alloc. Preferably, $Pg_1$ is selected from Alloc or acetyl.

The compound of formula (IV) is reacted with a suitable substituted compound of formula (V), wherein $R_{4a}$ is $R_4$ other than hydrogen and wherein J is Br, Cl, or I, a known compound or compound prepared by known methods, in the presence of a base such as NaH, n-butyl lithium, LDA, LHMDS, and the like, in a polar aprotic solvent such as THF, dioxane, MTBE, and the like, to yield the corresponding compound of formula (VI). The compound of formula (VI) is then reacted with $ClSO_3H$, optionally in a polar organic solvent which is inert to $ClSO_3H$, such as DCM, DCE, acetonitrile, DMF, to yield the corresponding compound of formula (VII).

Alternatively, the compound of formula (IV) is reacted with ClSO$_3$H, optionally in a polar organic solvent which is inert to ClSO$_3$H, such as DCM, DCE, acetonitrile, DMF, to yield the corresponding compound of formula (VII) wherein R$_4$ is hydrogen.

The compound of formula (VII) is reacted with a reducing agent capable of reducing the chlorosulfonyl group on the compound of formula (VII), such as Zn, and the like, in the presence of an acid such as HCl, H$_2$SO$_4$, and the like, in an aprotic solvent such as acetonitrile, THF, dioxane, and the like; or with Zn in the presence of (CH$_3$)$_2$SiCl$_2$ and DMA, in an aprotic organic solvent such as THF, dioxane, acetonitrile, 1,2-dichloroethane, and the like; to yield a mixture of the corresponding compound of formula (VII) and the corresponding compound of formula (IX).

Alternatively, wherein the compound of formula (VII) Pg$_1$ is tosyl or MTr, the compound of formula (VII) is reacted with a reducing agent capable of reducing the chlorosulfonyl group on the compound of formula (VII), such as LiAlH$_4$, and the like, in an organic solvent which is inert to the reducing agent, such as THF, dioxane, and the like, at a temperature in the range of from about room temperature to about reflux, preferably at about reflux, to yield the corresponding compound of formula (VIII).

The compound of formula (VIII), isolated or in a mixture with the compound of formula (IX) is reacted with a suitably substituted compound of formula (X), wherein W is Br, Cl or I, a known compound or compound prepared by known methods, in the presence of an organic base which is inert to the compound of formula (X), such as TEA, DIPEA, pyridine, and the like or in the presence of an inorganic base which is inert to the compound of formula (X), such as NaHCO$_3$, Na$_2$CO$_3$, K$_2$CO$_3$, Cs$_2$CO$_3$, and the like, in a polar aprotic solvent such as THF, dioxane, DMF, acetonitrile, and the like, to yield the corresponding compound of formula (XI).

Alternatively, the compound of formula (IX), isolated or in a mixture with the compound of formula (VII) is reacted with a reducing agent which is capable of reducing the disulfide on the compound of formula (VII), such as LiAlH$_4$, LiBH$_4$, NaBH$_4$, and the like, in an organic solvent which is inert to the reducing agent, such as THF, dioxane, and the like, at a temperature in the range of from about room temperature to about reflux, preferably at about room temperature, to yield the corresponding compound of formula (VIII), which is preferably not isolated. The compound of formula (VIII) is then reacted with a suitably substituted compound of formula (X), wherein W is Br, Cl or I, a known compound or compound prepared by known methods, in the presence of an organic base which is inert to the compound of formula (X), such as TEA, DIPEA, pyridine, and the like or in the presence of an inorganic base which is inert to the compound of formula (X), such as NaHCO$_3$, Na$_2$CO$_3$, K$_2$CO$_3$, Cs$_2$CO$_3$, and the like, in a polar aprotic solvent such as THF, dioxane, DMF, acetonitrile, and the like, to yield the corresponding compound of formula (XI).

The compound of formula (XI) is reacted to yield the corresponding compound of formula (L). For example, the compound of formula (XI) is de-protected according to known methods, such as those described in *Protective Groups in Organic Chemistry*, ed. J. F. W. McOmie, Plenun Pressm 1973 and T. W. Green and P. G. M. Wuts, *Protective Groups in Organic* Synthesis, John Wiley & Sons, 1991, to yield the corresponding compound of formula (L).

Compounds of formula (L) may alternatively be prepared according to the process outlined in Scheme 2.

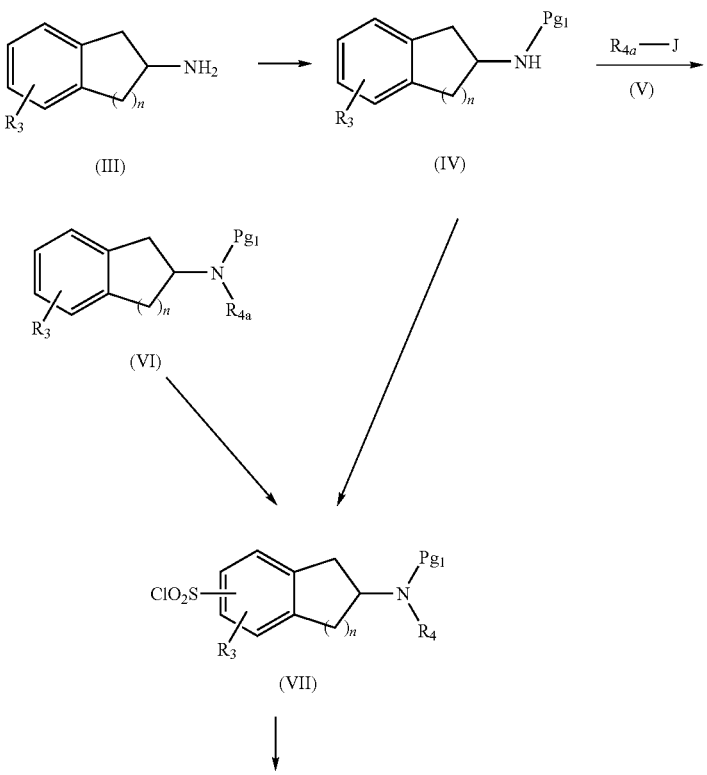

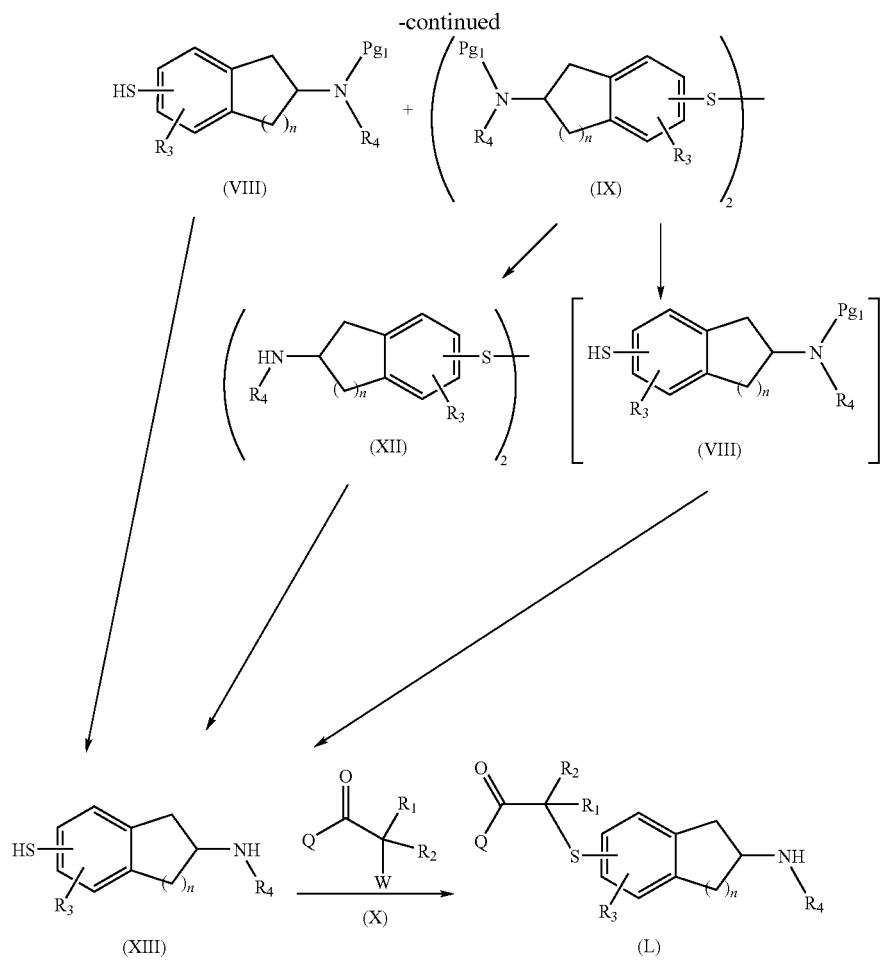

Accordingly, a suitably substituted compound of formula (III), a known compound or compound prepared by known methods, is reacted (for example, protected) according to known methods, to yield the corresponding compound of formula (IV), wherein $Pg_1$ is a nitrogen protecting group which is inert to $ClSO_3H$, such as, Alloc ($CH_2$=$CHCH_2$—O—C(O)—), acetyl ($CH_3$—C(O)—), ($C_{1-4}$alkyl)-C(O)—, and the like. For example, the compound of formula (III) is reacted with a suitably selected protecting reagent such as Alloc-Cl ($CH_2$=$CHCH_2$—O—C(O)—Cl), $Alloc_2O$ ($CH_2$=$CHCH_2$—OC(O)—O—C(O)O—$CH_2CH$=$CH_2$), AcCl ($CH_3$—C(O)—Cl), $Ac_2O$ ($CH_3$—C(O)—O—C(O)—$CH_3$), and the like. Wherein the compound of formula (III) is reacted with a Alloc-Cl, or $Alloc_2O$, the corresponding protecting group $Pg_1$ is Alloc. Preferably, $Pg_1$ is selected from Alloc or acetyl.

The compound of formula (IV) is reacted with a suitable substituted compound of formula (V), wherein $R_{4a}$ is $R_4$ other than hydrogen and wherein J is Br, Cl, or I, a known compound or compound prepared by known methods, in the presence of a base such as NaH, n-butyl lithium, LDA, LHMDS, and the like, in a polar aprotic solvent such as THF, dioxane, MTBE, and the like, to yield the corresponding compound of formula (VI). The compound of formula (VI) is then reacted with $ClSO_3H$, optionally in a polar organic solvent which is inert to $ClSO_3H$, such as DCM, DCE, acetonitrile, DMF, to yield the corresponding compound of formula (VII).

Alternatively, the compound of formula (IV) is reacted with $ClSO_3H$, optionally in a polar organic solvent which is inert to $ClSO_3H$, such as DCM, DCE, acetonitrile, DMF, to yield the corresponding compound of formula (VII) wherein $R_4$ is hydrogen.

The compound of formula (VII) is reacted with a reducing agent capable of reducing the chlorosulfonyl group on the compound of formula (VII), such as Zn, and the like, in the presence of an acid such as HCl, $H_2SO_4$, and the like, in an aprotic solvent such as acetonitrile, THF, dioxane, and the like; or with Zn in the presence of $(CH_3)_2SiCl_2$ and DMA, in an aprotic organic solvent such as THF, dioxane, acetonitrile, 1,2-dichloroethane, and the like; to yield a mixture of the corresponding compound of formula (VIII) and the corresponding compound of formula (IX).

Alternatively, wherein the compound of formula (VII) $Pg_1$ is tosyl or MTr, the compound of formula (VII) is reacted with a reducing agent capable of reducing the chlorosulfonyl group on the compound of formula (VII), such as $LiAlH_4$, and the like, in an organic solvent which is inert to the reducing agent, such as THF, dioxane, and the like, at a temperature in the range of from about room temperature to about reflux, preferably at about reflux, to yield the corresponding compound of formula (VIII).

The compound of formula (VIII), isolated or in a mixture with the compound of formula (IX), is de-protected according to known methods, such as those described in *Protective*

*Groups in Organic Chemistry*, ed. J. F. W. McOmie, Plenun Pressm 1973 and T. W. Green and P. G. M. Wuts, *Protective Groups in Organic* Synthesis, John Wiley & Sons, 1991, to yield the corresponding compound of formula (XIII).

Alternatively, the compound of formula (IX), isolated or in a mixture with the compound of formula (VIII), is reacted with a reducing agent which is capable of reducing the disulfide on the compound of formula (IX), such as $LiAlH_4$, $LiBH_4$, $NaBH_4$, and the like, in an organic solvent which is inert to the reducing agent, such as THF, dioxane, and the like, at a temperature in the range of from about room temperature to about reflux, preferably at about room temperature, to yield the corresponding compound of formula (VIII), which is preferably not isolated. The compound of formula (VIII) is then de-protected according to known methods, such as those described in *Protective Groups in Organic Chemistry*, ed. J. F. W. McOmie, Plenun Pressm 1973 and T. W. Green and P. G. M. Wuts, *Protective Groups in Organic* Synthesis, John Wiley & Sons, 1991, to yield the corresponding compound of formula (XIII).

Alternatively still, the compound of formula (IX), isolated or in a mixture with the compound of formula (VIII), is de-protected according to known methods, such as those described in *Protective Groups in Organic Chemistry*, ed. J. F. W. McOmie, Plenun Pressm 1973 and T. W. Green and P. G. M. Wuts, *Protective Groups in Organic Synthesis*, John Wiley & Sons, 1991, to yield the corresponding compound of formula (XII). The compound of formula (XII) is then reacted with a reducing agent which is capable of reducing the disulfide on the compound of formula (XII), such as $LiAlH_4$, $LiBH_4$, $NaBH_4$, and the like, in an organic solvent which is inert to the reducing agent, such as THF, dioxane, and the like, at a temperature in the range of from about room temperature to about reflux, preferably at about room temperature, to yield the corresponding compound of formula (XIII).

The compound of formula (XIII) reacted with a suitably substituted compound of formula (X), wherein W is Br, Cl or I, a known compound or compound prepared by known methods, in the presence of an organic base which is inert to the compound of formula (X), such as TEA, DIPEA, pyridine, and the like or in the presence of an inorganic base which is inert to the compound of formula (X), such as $NaHCO_3$, $Na_2CO_3$, $K_2CO_3$, $Cs_2CO_3$, and the like, in a polar aprotic solvent such as THF, dioxane, DMF, acetonitrile, and the like, to yield the corresponding compound of formula (L).

Compounds of formula (L) wherein $R_4$ is other than hydrogen may alternatively be prepared according to the process outlined in Scheme 3.

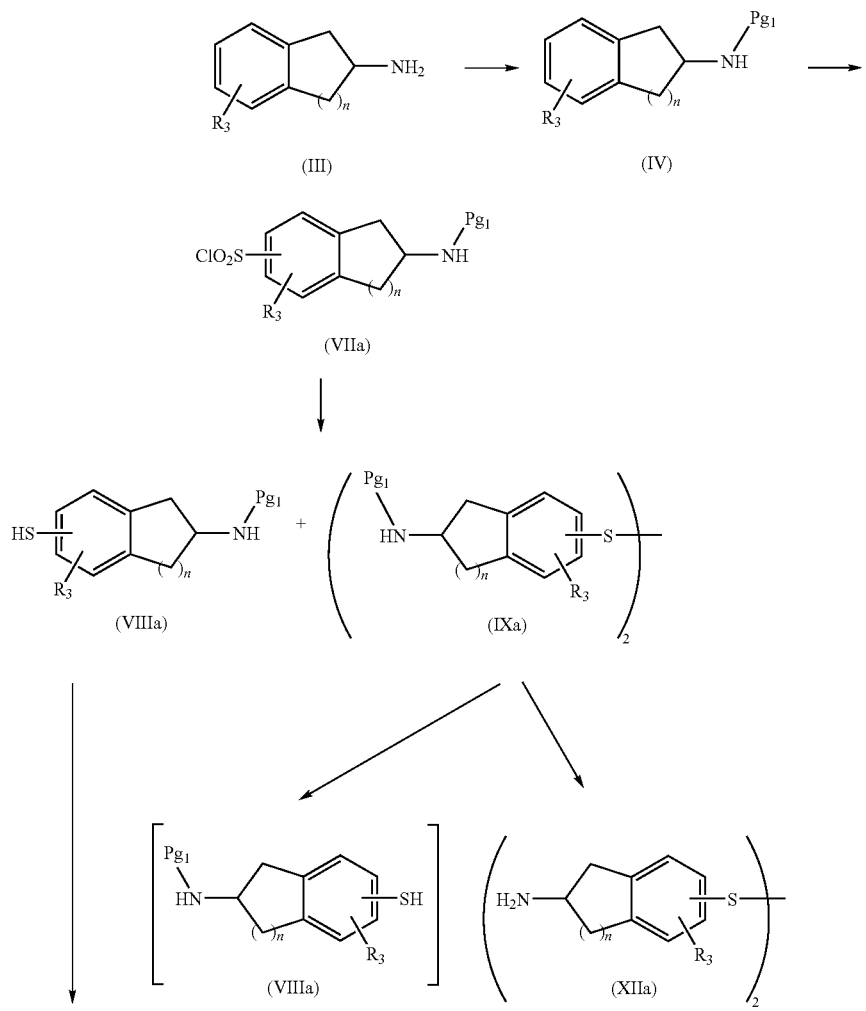

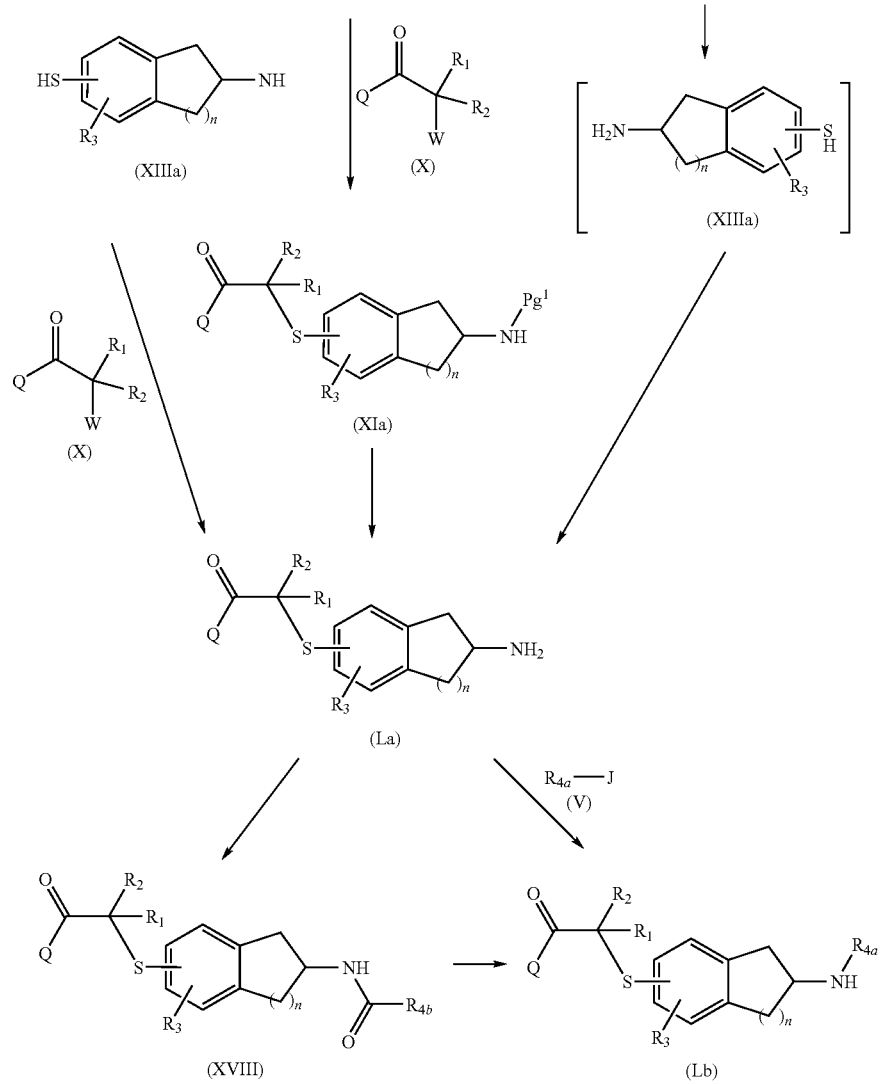

Accordingly, a suitably substituted compound of formula (III), a known compound or compound prepared by known methods, is reacted (for example, protected) according to known methods, to yield the corresponding compound of formula (IV), wherein $Pg_1$ is a nitrogen protecting group which is inert to $ClSO_3H$, such as, Alloc ($CH_2$=$CHCH_2$—O—C(O)—), acetyl ($CH_3$—C(O)—), ($C_{1-4}$alkyl)-C(O)—, and the like. For example, the compound of formula (III) is reacted with a suitably selected protecting reagent such as Alloc-Cl ($CH_2$=$CHCH_2$—O—C(O)—Cl), $Alloc_2O$ ($CH_2$=$CHCH_2$—OC(O)—O—C(O)O—$CH_2CH$=$CH_2$), AcCl ($CH_3$—C(O)—Cl), $Ac_2O$ ($CH_3$—C(O)—O—C(O)—$CH_3$), and the like. Wherein the compound of formula (III) is reacted with a Alloc-Cl, or $Alloc_2O$, the corresponding protecting group $Pg_1$ is Alloc. Preferably, $Pg_1$ is selected from Alloc or acetyl.

The compound of formula (IV) is reacted with $ClSO_3H$, optionally in a polar organic solvent which is inert to $ClSO_3H$, such as DCM, DCE, acetonitrile, DMF, to yield the corresponding compound of formula (VIIa) (i.e. the corresponding compound of formula (VII) wherein $R^4$ is hydrogen.).

The compound of formula (VIIa) is reacted with a reducing agent capable of reducing the chlorosulfonyl group on the compound of formula (VIIa) such as Zn, and the like, in the presence of an acid such as HCl, $H_2SO_4$, and the like, in an aprotic solvent such as acetonitrile, THF, dioxane, and the like; or with Zn in the presence of $(CH_3)_2SiCl_2$ and DMA, in an aprotic organic solvent such as THF, dioxane, acetonitrile, 1,2-dichloroethane, and the like; to yield a mixture of the corresponding compound of formula (VIIIa) (i.e. the corresponding compound of formula (VIII) wherein $R^4$ is hydrogen) and the corresponding compound of formula (IXa) (i.e. the corresponding compound of formula (IXa) wherein $R_4$ is hydrogen).

The compound of formula (VIIIa), isolated or in a mixture with the compound of formula (IXa) is de-protected according to known methods, such as those described in *Protective Groups in Organic Chemistry*, ed. J. F. W. McOmie, Plenun Pressm 1973 and T. W. Green and P. G. M. Wuts, *Protective Groups in Organic* Synthesis, John Wiley & Sons, 1991, to yield the corresponding compound of formula (XIIIa) (i.e. the corresponding compound of formula (XIII) wherein $R_4$ is hydrogen). The compound of formula (XIIIa) is reacted with a suitably substituted compound of formula (X), wherein W is Br, Cl or I, a known compound or compound prepared by known methods, in the presence of an organic base which is inert to the compound of formula (X), such as TEA, DIPEA, pyridine, and the like or in the presence of an inorganic base which is inert to the compound of formula (X), NaHCO$_3$, Na$_2$CO$_3$, K$_2$CO$_3$, Cs$_2$CO$_3$, and the like, in a polar aprotic solvent such as THF, dioxane, DMF, acetonitrile, and the like, to yield the corresponding compound of formula (La) (i.e. the corresponding compound of formula (L) wherein R$_4$ is hydrogen).

Alternatively, the compound of formula (IXa), isolated or in a mixture with the compound of formula (VIIIa), is reacted with a reducing agent which is capable of reducing the disulfide on the compound of formula (IXa), such as LiAlH$_4$, LiBH$_4$, NaBH$_4$, and the like, in an organic solvent which is inert to the reducing agent, such as THF, dioxane, and the like, at a temperature in the range of from about room temperature to about reflux, preferably at about room temperature, to yield the corresponding compound of formula (VIIIa). The compound of formula (VIIIa) is then reacted with a suitably substituted compound of formula (X), wherein W is Br, Cl or I, a known compound or compound prepared by known methods, in the presence of an organic base which is inert to the compound of formula (X), such as TEA, DIPEA, pyridine, and the like or in the presence of an inorganic base which is inert to the compound of formula (X), NaHCO$_3$, Na$_2$CO$_3$, K$_2$CO$_3$, Cs$_2$CO$_3$, and the like, in a polar aprotic solvent such as THF, dioxane, DMF, acetonitrile, and the like, to yield the corresponding compound of formula (XIa) (i.e. the corresponding compound of formula (XI) wherein R$_4$ is hydrogen). The compound of formula (XIa) is then reacted to yield the corresponding compound of formula (La). For example, the compound of formula (XIa) is de-protected according to known methods, such as those described in *Protective Groups in Organic Chemistry*, ed. J. F. W. McOmie, Plenun Pressm 1973 and T. W. Green and P. G. M. Wuts, *Protective Groups in Organic Synthesis*, John Wiley & Sons, 1991, to yield the corresponding compound of formula (La).

Alternatively still, the compound of formula (IXa), isolated or in a mixture with the compound of formula (VIIIa), is de-protected according to known methods, such as those described in *Protective Groups in Organic Chemistry*, ed. J. F. W. McOmie, Plenun Pressm 1973 and T. W. Green and P. G. M. Wuts, *Protective Groups in Organic Synthesis*, John Wiley & Sons, 1991, to yield the corresponding compound of formula (XIIa) (i.e. the corresponding compound of formula (XII) wherein R$_4$ is hydrogen). The compound of formula (XIIa) is then reacted with a reducing agent which is capable of reducing the disulfide on the compound of formula (XIIa), such as LiAlH$_4$, LiBH$_4$, NaBH$_4$, and the like, in an organic solvent which is inert to the reducing agent, such as THF, dioxane, and the like, at a temperature in the range of from about room temperature to about reflux, preferably at about room temperature, to yield the corresponding compound of formula (XIIIa) (i.e. the corresponding compound of formula (XIII) wherein R$_4$ is hydrogen). The compound of formula (XIIIa) is then reacted with a suitably substituted compound of formula (X), wherein W is Br, Cl or I, a known compound or compound prepared by known methods, in the presence of an organic base which is inert to the compound of formula (X), such as TEA, DIPEA, pyridine, and the like or in the presence of an inorganic base which is inert to the compound of formula (X), such as NaHCO$_3$, Na$_2$CO$_3$, K$_2$CO$_3$, Cs$_2$CO$_3$, and the like, in a polar aprotic solvent such as THF, dioxane, DMF, acetonitrile, and the like, to yield the corresponding compound of formula (La).

The compound of formula (La) is reacted with a suitably substituted compound of formula (V), wherein R$_{4a}$ is R$_4$ other than hydrogen and wherein J is Br, Cl, or I, a known compound or compound prepared by known methods, in the presence of a base such as NaH, n-butyl lithium, LDA, LHMDS, and the like, in a polar aprotic solvent such as THF, dioxane, MTBE, and the like, to yield the corresponding compound of formula (Lb).

Alternatively, the compound of formula (La) is reacted with a suitably substituted acylating agent capable of attaching an —C(O)—R$_{4b}$ group onto the nitrogen of the compound of formula (La), wherein R$_{4b}$ is selected from (C$_{1-4}$ straight chain alkylene)R$_{15}$ or (straight chain C$_{1-4}$alkylene)R$_{16}$, in the presence of an organic such as TEA, DIPEA, pyridine, and the like, or in the presence of an inorganic base such as NaHCO$_3$, Na$_2$CO$_3$, K$_2$CO$_3$, Cs$_2$CO$_3$, and the like, in a polar aprotic solvent such as THF, dioxane, DMF, acetonitrile, and the like, to yield the corresponding compound of formula (XVIII); the compound of formula (XVIII) is then reacted with a reducing agent capable of reducing the amide on the compound of formula (XVIII), such as borane, and the like, in a aprotic organic solvent such as THF, dioxane, MTBE, and the like, to yield the corresponding compound of formula (Lb).

Compounds of formula (L) wherein R$_4$ is other than hydrogen, (C$_1$ straight chain alkylene)R$_{15}$ or (straight chain C$_1$alkylene)R$_{16}$ may be prepared according to the process outlined in Scheme 4.

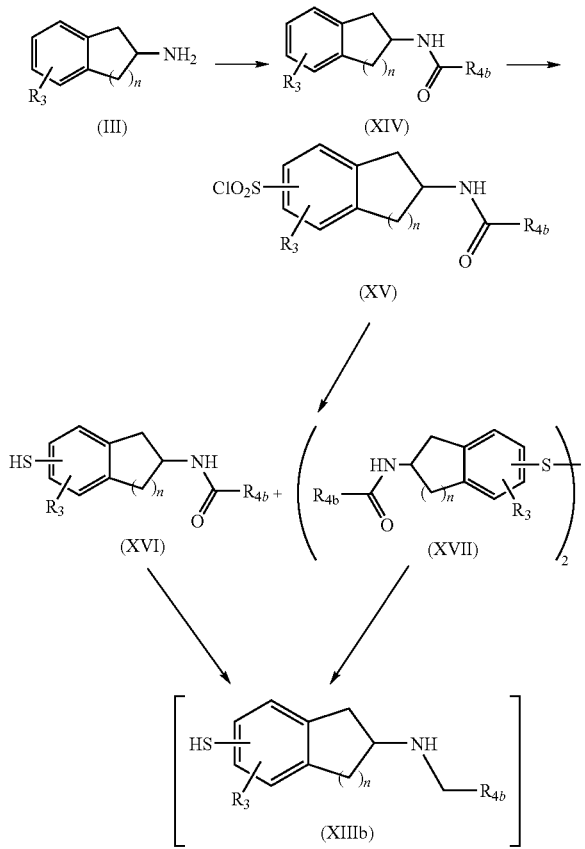

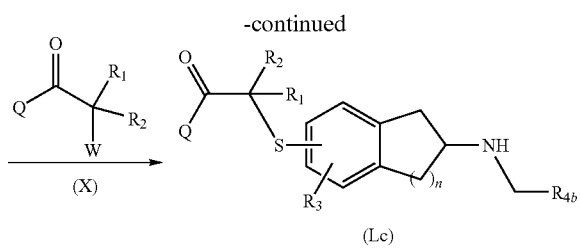

Accordingly, a suitably substituted compound of formula (III), a known compound or compound prepared by known methods, is reacted with a suitably substituted acylating capable of attaching an —C(O)O—$R_{4b}$ group onto the nitrogen of the compound of formula (III), wherein $R_{4b}$ is selected from ($C_{1-4}$ straight chain alkylene)$R_{15}$ or (straight chain $C_{1-4}$ alkylene)$R_{16}$, for example an acid chloride of the formula Cl—C(O)—$R_{4b}$, a symmetric anhydride of the formula $R_{4b}$—C(O)—O—C(O)—$R_{4b}$, and the like, in the presence of an organic base, preferably a tertiary amine base such as TEA, DIPEA, pyridine, and the like, in an aprotic solvent such as THF, DMF, dioxane, ethyl acetate, and the like; or in the presence of an organic or inorganic base such as NaOH, KOH, $Na_2CO_3$, $NaHCO_3$, $K_2CO_3$, $KHCO_3$, TEA, DIPEA, pyridine, and the like, in a mixture of an aprotic solvent and water, to yield the corresponding compound of formula (XIV).

The compound of formula (XIV) is reacted with $ClSO_3H$, optionally in a polar organic solvent which is inert to $ClSO_3H$, such as DCM, DCE, acetonitrile, DMF, to yield the corresponding compound of formula (XV).

The compound of formula (XV) is reacted with a reducing agent capable of reducing the chlorosulfonyl group on the compound of formula (XV), such as Zn, and the like, in the presence of an acid such as HCl, $H_2SO_4$, and the like, optionally in an aprotic solvent such as acetonitrile, THF, dioxane, and the like; or with Zn in the presence of $(CH_3)_2SiCl_2$ and DMA, in an aprotic organic solvent such as THF, dioxane, acetonitrile, 1,2-dichloroethane, and the like; to yield a mixture of the compound of formula (XVI) and the compound of formula (XVII).

One skilled in the art will recognize that when the compound of formula (XV) is reacted with a reducing agent capable of reducing the chlorosulfonyl group and the amide group on the compound of formula (XV), such as $LiAlH_4$, and the like, in an organic solvent which is inert to the reducing agent, such as THF, dioxane, and the like, at a temperature in the range of from about room temperature to about reflux, preferably at about reflux, then the compound of formula (XV) is reacted to yield the corresponding compound of formula (XIIIb) in one step.

The compound of formula (XVI), isolated or in a mixture with the compound of formula (XVII) is reacted with a reducing agent which is capable of reducing the amide on the compound of formula (XVI), such as $LiAlH_4$, borane, and the like, in an aprotic solvent which is inert to the reducing agent, such as THF, dioxane, and the like, to yield the corresponding compound of formula (XIIIb) (i.e. the corresponding compound of formula (XIII) wherein $R_4$ is other than hydrogen). Wherein the reducing agent is $LiAlH_4$, the compound(s) is reduced at a temperature in the range of from about room temperature to about reflux, preferably at about room temperature.

Alternatively, the compound of formula (XVII), isolated or in a mixture with the compound of formula (XVI) is reacted with a reducing agent which is capable of reducing the amide on the compound of formula (XVII) and the disulfide on the compound of formula (XVII), such as $LiAlH_4$, borane, and the like, in an aprotic solvent which is inert to the reducing agent, such as THF, dioxane, and the like, to yield the corresponding compound of formula (XIIIb). Wherein the reducing agent is $LiAlH_4$, the compound(s) is reduced at a temperature in the range of from about room temperature to about reflux, preferably at about room temperature.

The compound of formula (XIIIb) is reacted with a suitably substituted compound of formula (X), wherein W is Br, Cl or I, a known compound or compound prepared by known methods, in the presence of an organic base which is inert to the compound of formula (X), such as TEA, DIPEA, pyridine, and the like or in the presence of an inorganic base which is inert to the compound of formula (X), such as $NaHCO_3$, $Na_2CO_3$, $K_2CO_3$, $Cs_2CO_3$, and the like, in a polar aprotic solvent such as THF, dioxane, DMF, acetonitrile, methanol, ethanol, and the like, to yield the corresponding compound of formula (Lc) (i.e. the corresponding compound of formula (L) wherein $R_4$ is selected from ($C_{2-5}$ straight chain alkylene)$R_{15}$ or (straight chain $C_{2-5}$ alkylene)$R_{16}$).

The present invention is further directed to a process for the preparation of compounds of formula (I)

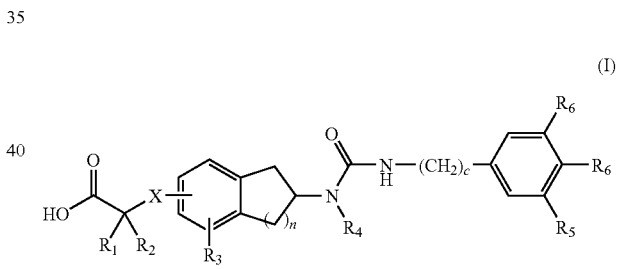

wherein $R_1$, $R_2$, X, $R_3$, n, $R_4$, c, $R_5$, $R_6$ and $R_7$ are as herein defined. The compounds of formula (I) are useful as PPAR alpha agonists, more specifically as selective PPAR alpha agonists. PPAR alpha agonists are useful for the treatment, prevention, or inhibiting the progression of one or more of the following conditions or diseases: phase I hyperlipidemia; pre-clinical hyperlipidemia; phase II hyperlipidemia; hypertension; CAD (coronary artery disease); coronary heart disease; hypertriglyceridemia; lowering serum levels of low-density lipoproteins (LDL), IDL, and/or small-density LDL and other atherogenic molecules, or molecules that cause atherosclerotic complications, thereby reducing cardiovascular complications; elevating serum levels of high-density lipoproteins (HDL); lowering serum levels of triglycerides, LDL, and/or free fatty acids; and/or lowering FPG/HbA1c.

More specifically, the compound of formula (I) may be prepared by reacting a suitably substituted compound of formula (L) with a suitably substituted isocyanate, a compound of the formula (XIX)

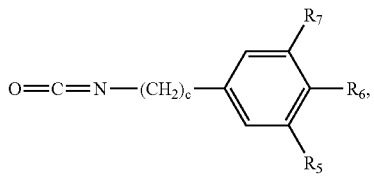

(XIX)

according to known methods. One skilled in the art will recognize that in reacting the compound of formula (L) with a suitably substituted isocyanate, a compound of formula (XIX), it may be necessary or desirable to protect reactive groups on the compound of formula (L), according to known methods. For example, it may be necessary or desirable to protect the carboxylic acid or amide on the compound of formula (L) when Q is OH or $NH_2$, respectively. One skilled in the art will further recognize that wherein the compound of formula (L) Q is $OPg^2$, NH or $N(Pg^3Pg^4)$, the compound of formula (L) is reacted with a suitably substituted isocyanate, a compound of formula (XIX), according to known methods, to yield an intermediate which is then de-protected according to known methods to yield the corresponding compound of formula (I).

In an embodiment of the present invention is a process for the preparation of a compound of formula (L) wherein X is S, $R_1$ is methyl, $R_2$ is methyl, Q is OH or $OPg^2$, the —X—C($R_1R_2$)—C(O)-Q is bound at the 5-position, $R_3$ is hydrogen, n is 1 and $R_4$ is ethyl. In another embodiment of the present invention is a process for the preparation of a compound of formula (L) wherein X is S, $R_1$ is methyl, $R_2$ is methyl, Q is $OPg^2$, $Pg^2$ is t-butyl, the —X—C($R_1R_2$)—C(O)-Q is bound at the 5-position, $R_3$ is hydrogen, n is 1 and $R_4$ is ethyl.

In another embodiment of the present invention is a process for the preparation of a compound of formula (I) or a pharmaceutically acceptable salt, $C_{1-6}$ester or $C_{1-6}$amide thereof, wherein X is S, $R_1$ is methyl, $R_2$ is methyl, wherein —X—C($R_1R_2$)—C(O)—OH is bound at the 5-position, $R_3$ is hydrogen, n is 1, $R_4$ is ethyl, c is 0, $R_5$ is hydrogen, $R_6$ is trifluoromethoxy and $R_7$ is hydrogen.

The present invention is further directed to a process for the preparation of the compound of formula (Le)

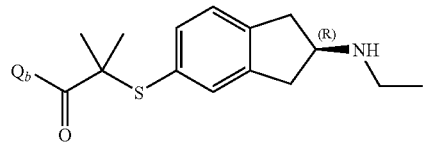

(Le)

wherein $Q_b$ is selected from the group consisting of $C_{1-6}$alkoxy, wherein the $C_{1-6}$alkoxy is not substituted with amino. Preferably, $Q_b$ is unsubstituted $C_{1-6}$alkoxy, more preferably, $Q_b$ is selected from the group consisting of methoxy, ethoxy and t-butoxy.

More specifically, the compound of formula (Le) may be prepared according to the process outlined in Scheme 5.

Scheme 5

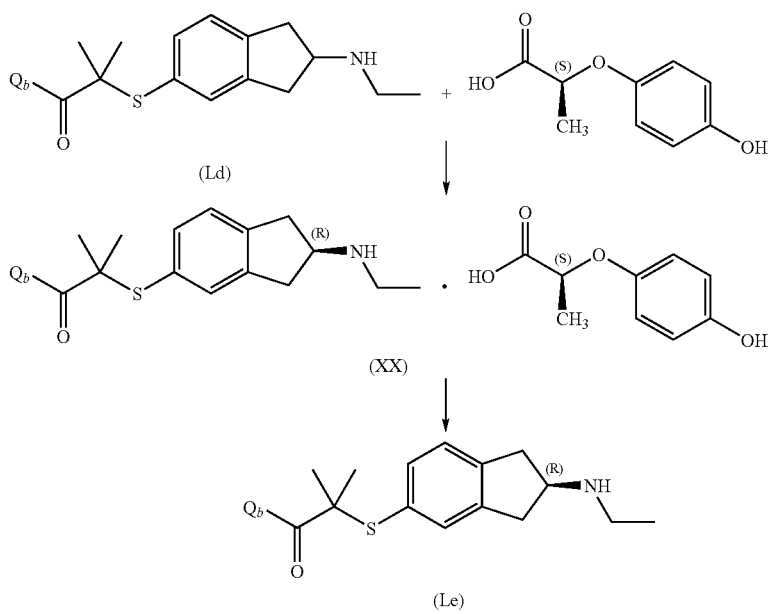

Accordingly, a compound of formula (Ld) is reacted with (S)-2-(4-hydroxyphenoxy)propionic acid, in an alcohol such as methanol, ethanol, and the like, preferably ethanol; or in acetone, at a temperature in the range of from about 35° C. to about 0° C., to yield the corresponding (R,S) diastereomeric salt, the compound of formula (XX).

The (R,S) diastereomeric salt, the compound of formula (XX), is reacted with an inorganic base such as NaOH, KOH, $Na_2CO_3$, $K_2CO_3$, and the like to yield the corresponding compound of formula (Le).

Preferably, the compound of formula (Le) is prepared with an enantiomeric excess in the range of from about 70% ee to about 90% ee. One skilled in the art will recognize that wherein a greater % ee is desired, the diastereomeric salt of the compound of formula (Le) may be further re-slurrried in or recrystallized from an organic solvent such as methanol, ethanol, acetone, and the like.

The compound of formula (Le) may alternatively be prepared according to the process outlined in Scheme 6.

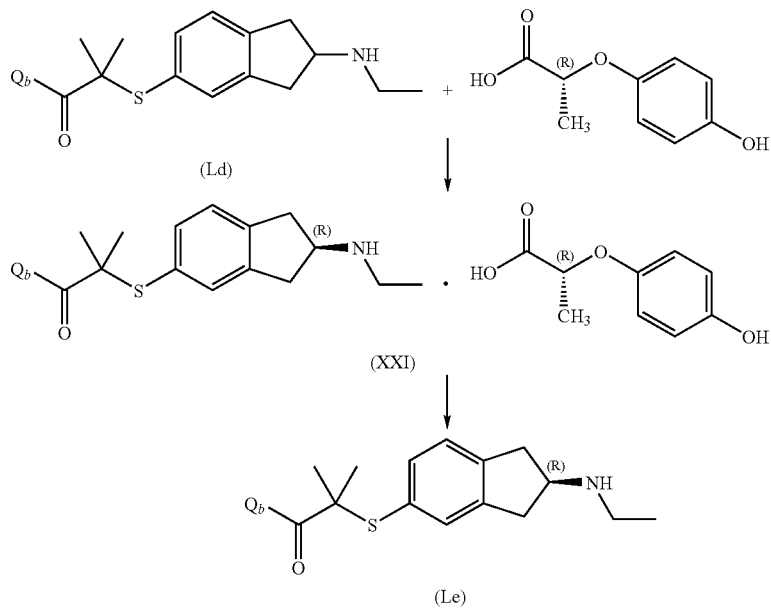

Accordingly, a compound of formula (Ld) is reacted with (R)-2-(4-hydroxyphenoxy)propionic acid, in acetone, at a temperature greater than about 35° C., preferably at a temperature greater than about 45° C.; or in THF at about room temperature; to yield the corresponding (R,R) diastereomeric salt, the compound of formula (XXI).

The (R,R) diastereomeric salt, the compound of formula (XXI), is reacted with an inorganic base such as NaOH, KOH, $Na_2CO_3$, $K_2CO_3$, and the like to yield the corresponding compound of formula (Le).

Preferably, the compound of formula (Le) is prepared with an enantiomeric excess in the range of from about 70% ee to about 90% ee. One skilled in the art will recognize that wherein a greater % ee is desired, the diasteromeric salt of the compound of formula (Le) may be further re-slurrried in or recrystallized from an organic solvent such as methanol, ethanol, acetone, and the like.

One skilled in the art will further recognize that the S-enantiomer of the compound of formula (Ld), a compound of formula (Lf)

may be similarly prepared by reacting a compound of formula (Ld) with (R)-2-(4-hydroxyphenoxy)propionic acid, in an alcohol such as methanol, ethanol, and the like, preferably ethanol; or in acetone, at a temperature in the range of from about 35° C. to about 0° C.; to yield the corresponding (S,R) diastereomeric salt which is then reacted with an inorganic base such as NaOH, KOH, $Na_2CO_3$, $K_2CO_3$, and the like, to yield the corresponding compound of formula (Lf).

Alternatively, the S-enantiomer of the compound of formula (Ld) (i.e. the compound of formula (Lf)) may be prepared by reacting a compound of formula (Ld) with (S)-2-(4-hydroxyphenoxy)propionic acid, in acetone, at a temperature greater than about 35° C., preferably at a temperature greater than about 45° C.; or in THF at about room temperature; to yield the corresponding (S,S) diastereomeric salt which is then reacted with an inorganic base such as NaOH, KOH, $Na_2CO_3$, $K_2CO_3$, and the like, to yield the corresponding compound of formula (Lf).

The present invention is further directed to a novel crystalline salt of the compound of formula (IIa)

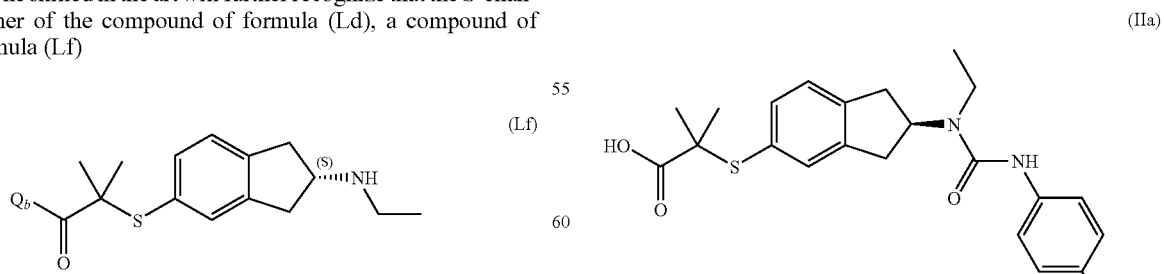

more specifically a crystalline N,N'-dibenzylethylenediamine (benzathine) salt of the compound of formula (IIa). In an embodiment of the present invention is a crystalline N,N'-dibenzylethylenediamine salt of the compound of formula (IIa) wherein the ratio of the compound of formula (IIa) to the N,N'-dibenzylethylenediamine is 1:1.

The crystalline benzathine salt of the compound of formula (IIa) may be characterized by the major peaks of its X-ray diffraction peaks, as listed in Table 1, below. The X-ray diffraction pattern was measured as follows. The crystalline benzathine salt of the compound of formula (IIa) was back-loaded into a conventional X-ray holder. Using an X-Celerator detector, the sample was scanned from 3 to 35 °2θ at a step size of 0.0165 °2θ and a time per step of 10.16 seconds. The effective scan speed was 0.2067°/s. Instrument voltage and current settings of 45 kV and 40 mA were employed.

TABLE 1

XRD - Compound of formula (IIa) Benzathine Salt

| Position [°2θ] | d-spacing [Å] | Relative Intensity [%] |
|---|---|---|
| 6.3894 | 13.8336 | 17.39 |
| 8.0423 | 10.9938 | 13.38 |
| 12.157 | 7.2803 | 19.22 |
| 16.012 | 5.5354 | 15.74 |
| 17.929 | 4.9475 | 20.77 |
| 18.048 | 4.9151 | 14.20 |
| 19.038 | 4.6618 | 100.00 |
| 19.2656 | 4.6072 | 26.28 |
| 20.325 | 4.3694 | 10.65 |
| 21.943 | 4.0508 | 16.85 |
| 22.190 | 4.0063 | 18.63 |
| 22.330 | 3.9815 | 12.37 |

The present invention is further directed to a process for the preparation of the benzathine salt of the compound of formula (IIa). More particularly, the compound of formula (IIa) is reacted with N,N'-dibenzylethylenediamine, in an aprotic solvent such as isopropyl acetate, ethyl acetate, MTBE, and the like, preferably in isopropyl acetate, preferably, at a temperature less than about 5° C., more preferably, at a temperature in the range of from about 5° C. to about −5° C., yield the corresponding N,N'-dibenzylethylenediame (benzathine) salt of the compound of formula (IIa).

The following Examples are set forth to aid in the understanding of the invention, and are not intended and should not be construed to limit in any way the invention set forth in the claims which follow thereafter.

EXAMPLE 1

N-Indan-2-yl-acetamide

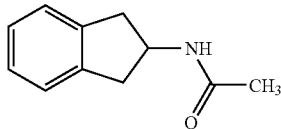

To a cooled mixture of 2-aminoindan (1.2 mol, 160.00 g) in ethyl acetate (1019 mL) at about 5-7° C. was added a solution of $Na_2CO_3$ (2.4 mol, 254.65 g) in water (1528 mL) while stirring, followed by the addition of a solution of acetyl chloride (1.32 mol, 109.19 g) slowly over 2 hours. The reaction temperature was maintained below 10° C. by adjusting the addition rate. During the addition, a suspension was formed. After the addition of acetyl chloride, the mixture was stirred at the room temperature for 1 hour. The precipitated solid was collected by vacuum filtration and the filter cake was washed with water (200 mL), EtOAc (200 mL), and air-dried for 48 hours. The first crop of the product was obtained as a white crystalline solid.

The filtrate was placed in a separatory funnel and the aqueous layer was separated. The organic layer was washed once with water (500 mL) and once with brine (500 mL). The ethyl acetate layer was evaporated in vacuo to half of its original volume and then diluted with heptane (1000 mL) while stirring to produce a white suspension. The solid was collected by vacuum filtration and washed twice with portions of heptane (300 mL). The second crop of the product was obtained as white crystalline solid.

mp 127-129° C.

$^1$H NMR (300 MHz, $CDCl_3$) δ 7.13 (m, 4H), 6.99 (br d, 1H), 4.57 (m, 1H), 3.19 (dd, J=16.1, 7.3 Hz, 2H), 2.78 (dd, J=16.0, 5.1 Hz, 2H), 1.85 (s, 3H).

$^{13}$C NMR (300 MHz, $CDCl_3$) δ 170.7, 141.4, 127.01, 125.1, 51.0, 41.2, 23.5.

MS (ESI): m/z 176.2 ($MH^+$).

Elemental Analysis for $C_{11}H_{13}NO$:

Calculated: C, 75.40; H, 7.48; N, 7.99. Found: C, 75.13; H, 7.73; N, 7.96.

EXAMPLE 2

2-Acetylamino-indan-5-sulfonyl chloride

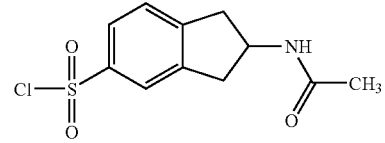

To a 2 L 3-necked glass reaction flask equipped with stirrer, condenser, thermocouple, 500 mL addition funnel and nitrogen inlet was added N-acetyl-2-aminoindan (0.96 mol, 167.70 g) and acetonitrile (490 mL). The reaction mixture was stirred and cooled in an ice-bath to about 3-5° C. and $ClSO_3H$ (3.83 mol, 440 g) was added slowly. The first 30% of the reagent was added over 30 minutes while maintaining the reaction temperature below 15° C. The ice-bath was then removed and the reaction mixture was warmed to room temperature. The remaining 70% of the reagent was added over 30 minutes and the temperature of the reaction solution rose to 80° C. at the end of the addition. The yellow reaction solution was stirred at 50° C. for about 20 hours. The reaction solution was cooled to 30° C. and slowly poured into a vigorously stirred mixture of ice (1620 g), water (945 mL), and acetonitrile (135 mL) in an ice-bath over about 10-15 minutes. The temperature of the quenching mixture dropped from 5° C. to −6° C. A white solid precipitated and the mixture was stirred at about 0-5° C. for 30 minutes. The solid was collected by vacuum filtration and slurried 4 times with a cold mixture of water (4×300 mL). The pH of the last slurry was around 2-3. The solid was then slurried with cold acetone (300 mL) (5-7° C.), collected by filtration, and finally rinsed with of cold acetone (200 mL). The solid product was air-dried for 4 hours, followed by drying in a vacuum oven at room temperature for 48 hours. The product was obtained as a white solid.

mp 158-160° C.

$^1$H NMR (300 MHz, DMSO-d$^6$) δ 8.53 (br s, 1H), 7.45 (s, 1H), 7.44 (d, J=7.8 Hz, 1H), 7.15 (d, J=7.8 Hz, 1H), 4.45 (br m, 1H), 3.15 (m, 2H), 2.77 (dd, J=16.2, 5.7 Hz, 2H), 1.85 (s, 3H).

$^{13}$C NMR (300 MHz, DMSO-d$^6$) δ 169.6, 145.3, 142.3, 140.9, 123.9, 123.7, 121.6, 50.2, 38.6, 38.4, 22.2.

MS (ESI): m/z 274.0 (MH$^+$)

Elemental Analysis for $C_{11}H_{12}ClNO_3S\cdot 0.1H_2O$:

Calculated: C, 47.95; H, 4.47; Cl, 12.87; N, 5.09; S, 11.64; KF, 0.66%. Found: C, 47.61; H, 4.49; Cl, 12.50; N, 5.13; S, 11.50; KF, 0.67%.

EXAMPLE 3

N-(5-Mercapto-indan-2-yl)-acetamide

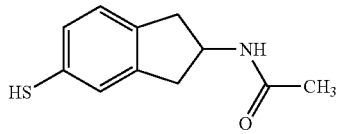

A suspension of zinc (22.94 g, 0.35 mol) and 2-acetylamino-indan-5-sulfonyl chloride (93% weight) (29.45 g, 0.10 mol) in acetonitrile (200 mL) in a 1 Liter four-necked round-bottomed flask equipped with a condenser, a thermometer, an addition funnel, and a mechanical stirrer was heated to about 50-60° C. The heating source was removed and to the warm suspension was added concentrated HCl (59.20 g, 0.60 mol) slowly over 1 hour. The addition rate was adjusted to maintain the reaction temperature between about 70-75° C. A gentle gas (H$_2$) evolution was observed throughout the addition of HCl. The reaction was then cooled to about 30-36° C. over 30 minutes while stirring. The reaction mixture was filtered into a 500 mL one-necked round-bottomed flask through a fritted glass funnel to remove the Zn residue. The reaction flask was rinsed with EtOAc (25 mL). The mixture was concentrated on a rotavapor under reduced pressure at about 45-50° C. bath temperature to remove most of the organic solvents. The concentrated aqueous solution was mixed with of EtOAc (150 mL), followed by the addition of H$_2$O (75 mL). After stirring for 15 minutes, the layers were separated. The organic layer was washed four times with H$_2$O (3×75 mL). After separation of layers, the organic layer was concentrated on a rotavapor at 60° C. to ¼ of its original volume (about 40 mL). Most of the precipitated white solid was dissolved by heating to reflux. The mixture was then diluted with MTBE (75 mL). The mixture was stirred at ambient temperature for 18 hours. The solid product was collected by vacuum filtration, washed with MTBE (20 mL), dried under nitrogen for 4 hours, then in a vacuum oven at about 40-45° C. for 24 h. The product was obtained as an off-white solid.

mp 128-129.5° C.

$^1$H NMR (300 MHz, DMSO-d$^6$) δ 8.12 (br d, J=6.6 Hz, 1H), 7.15 (s, 1H), 7.08 (br s, 2H), 5.18 (s, 1H), 4.41 (m, 1H), 3.09 (m, 2H), 2.69 (m, 2H), 1.79 (s, 3H).

$^{13}$C NMR (300 MHz, DMSO-d$^6$) δ 168.9, 142.4, 138.2, 129.2, 126.6, 125.0, 124.8, 49.9, 38.9, 38.5, 22.5.

MS (ESI): m/z 208.2 (MH$^+$)

Elemental Analysis for $C_{11}H_{13}NOS$:

Calculated: C, 63.73; H, 6.32; N, 6.76; S, 15.47. Found: C, 63.48; H, 6.50; N, 6.64; S, 15.56.

EXAMPLE 4

N-[5-(2-Acetylamino-indan-5-yldisulfanyl)-indan-2-yl]-acetamide

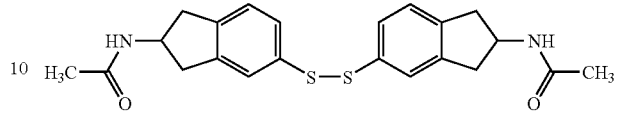

To a suspension of zinc (28.60 g, 0.44 mol) and 2-acetylamino-indan-5-sulfonyl chloride (40.00 g, 0.146 mol) in acetonitrile (400 mL) in a three-necked round-bottomed flask equipped with a magnetic stirrer, an addition funnel, and a thermometer was added a solution of dichlorodimethylsilane (44.2 mL, 0.365 mol) in acetonitrile (50 mL) at room temperature over 1 hour. The reaction temperature increased to 66° C. during the addition. After addition, the reaction mixture was stirred at room temperature for 20 hours and some solids were formed.

THF (100 mL) was added to dissolve the suspension and the excess Zn was removed by decantation and rinsed with THF (20 mL. The crude ACN/THF solution was extracted with heptane (3×300 mL) to remove the silane byproducts. The ACN/THF layer was concentrated and re-dissolved in EtOAc (300 mL) and H$_2$O (150 mL). The mixture was stirred for 10 minutes and the layers were separated. The organic layer was washed with H$_2$O (2×200 mL), brine (200 mL), and then concentrated to the half of its original volume. The solution was diluted with toluene (200 mL) and concentrated again to remove all EtOAc. The suspension in toluene was warmed to 90° C. for 15 minutes and stirred at room temperature for 20 hours. The solid product was collected by vacuum filtration, rinsed with toluene (20 mL), air-dried for 2 hours, and further dried in a vacuum oven at 60° C. for 2 days. The product was obtained as an off-white solid.

mp 165-168° C. (soften at 137° C.)

$^1$H NMR (300 MHz, DMSO-d$^6$) δ 8.13 (d, J=7.7 Hz, 2H), 7.38 (s, 2H), 7.30 (d, J=7.9 Hz, 2H), 7.22 (d, J=7.7 Hz, 2H), 4.42 (br m, 2H), 3.15 (m, 2H), 3.11 (m, 2H), 2.71 (dd, J=16.2, 5.3 Hz, 4H), 1.78 (s, 6H).

$^{13}$C NMR (300 MHz, DMSO-d$^6$) δ 168.8, 142.9, 141.4, 133.7, 126.1, 125.3, 124.0, 49.9, 38.9, 38.6, 22.5.

MS (ESI): m/z 413.1 (MH$^+$)

EXAMPLE 5 tert-Butyl 2-(2-ethylamino-indan-5-ylsulfanyl)-2-methyl-propionate

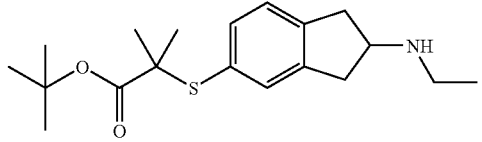

N-(5-Mercapto-indan-2-yl)-acetamide (330.0 g, 1.59 mol) was dissolved in a warm THF (1.65 L) at 50° C. The solution was then slowly added to LAH solution (1 M in THF) (2.385 L, 2.385 mol) at about 60-66° C. over 25 minutes to allow gentle reflux and slow gas evolution. After addition, the light yellow suspension was stirred under reflux for 4 hours. The reaction was cooled to about 5-7° C. in an ice-water bath. The reaction was quenched by the slow addition of methanol (203.7 g, 6.36 mol) under a nitrogen atmosphere and the reaction temperature was maintained below 25° C. by adjusting the addition rate. After quenching, the resulted green suspension was cooled to 5-7° C. and treated with tert-butyl 2-bromo-2-methylpropionate (354.7 g, 1.59 mol). The resulted mixture was warmed to room temperature while stirring and then maintained with stirring at room temperature for 2 hours. The reaction mixture was treated by the slow addition of $H_2O$ (90.6 mL) and 15% of aqueous NaOH (90.6 mL) sequentially. The resulted granular solid was removed by vacuum filtration through a 3 L coarse frit funnel lined with Celite filter aid. The filter cake was rinsed twice with THF (2×500 mL). The combined filtrate was concentrated in vacuo to remove about 70-80% of THF. The filter cake was suspended in EtOAc (2 L) and stirred for 30 minutes. The suspension was filtered through a 3 L coarse frit funnel. The filtrate was combined with the crude concentrated THF solution obtained above. The combined organic layer was washed with $H_2O$ (2 L). After separation of layers, the organic layer was concentrated in vacuo at 50° C. to remove the most of volatiles. The concentrated solution was diluted with anhydrous ethanol (800 mL) and re-concentrated to yield a purple oil. The crude product was used for the next step without further purification.

MS (ESI): m/z 336.1 (MH+)

EXAMPLE 6

(S)-2-(4-hydroxyphenoxy)propionic acid

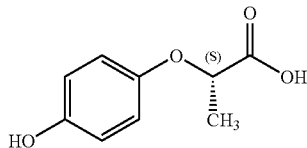

To (R)-2-chloropropionic acid (200 g, 1.81 mol) was added a solution of 50% NaOH (147.4 g, 1.84 mol) in water (520 mL) with the internal temperature below 25° C. In another flask, water (800 mL) and hydroquinone (811.8 g, 7.38 mol) were mixed. To the water/hydroquinone mixture was added 50% NaOH (1179.6 g, 14.71 mol), then the above (R)-2-chloropropionate sodium salt solution was added to the mixture, keeping the internal temperature below 55° C. The reaction mixture was heated at about 55-60° C. for an additional 2 h.

The reaction mixture was then cooled down to 5° C. To the reaction mixture was added concentrated HCl (1090 mL, 13.28 mol) while maintaining the temperature at about 15-30° C. to adjust the pH to about 4.3. The excess solid hydroquinone was removed by extraction with methyl isobutyl ketone three times (1200 mL, 200 mL×2). The resulting aqueous layer was further acidified to pH 1 with concentrated HCl (140 mL, 1.7 mol). Most of the (S)-2-(4-hydroxylphenoxy)propionic acid became solid at this point. (S)-2-(4-hydroxylphenoxy)propionic acid was then extracted into isopropyl acetate (800 mL and 400 mL). Water (325 mL) was added to the isopropyl acetate solution and the isopropyl acetate was removed azeotropically. The aqueous solution was adjusted to pH about 2.2 with 50% NaOH, then cooled down slowly to 20° C. The crude solid was collected by vacuum filtration and the filter cake was washed with small amount of water. The crude solid was recrystallized from water (230 mL) to yield the title compound as a white granular solid of 100% ee.

mp 139-140° C.

Optical rotation: $[\alpha]^{20}_D = -38.5$ (c 1.0, MeOH)

MS: m/z (ESI−): 181.12 (M-H)−, m/z (ESI+): 204.96 (M+Na)+

$^1$H NMR (300 MHz, DMSO-d$^6$) δ 12.85 (br s, 1H), 8.95 (br s, 1H), 6.68 (m, 4H), 4.62 (q, J=6.8 Hz, 1H), 1.44 (d, J=6.8 Hz, 3H).

$^{13}$C NMR (300 MHz, DMSO-d$^6$) δ 173.8, 151.9, 150.6, 116.4, 116.0, 72.7, 18.7,

FTIR (KBr): 3211 (br.), 1716, 1516, 1454, 1416, 1377, 1330, 1263, 1233, 1176, 1136, 1098, 1045, 946, 918, 861, 826, 766, 712, 697, 673, 638, 563, 508 cm$^{-1}$.

Elemental Analysis for $C_9H_{10}O_4$:
Calculated: C, 59.34; H, 5.93. Found: C, 59.24; H, 5.83.

EXAMPLE 7

(R)-(−)-tert-Butyl 2-(2-ethylamino-indan-5-ylsulfanyl)-2-methyl-propionate, (S)-(−)-2-(4-hydroxyphenoxy)propionic acid salt

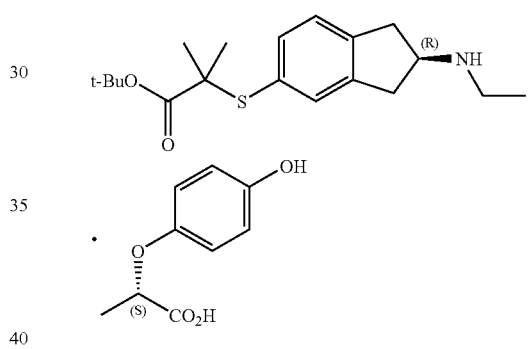

A solution of (S)-(−)-2-(4-hydroxyphenoxy)propionic acid (46.7 g) in 95% EtOH (200 mL) was warmed to about 30-35° C. To the solution was added a solution of the crude dark purple oil prepared in Example 5 above (94.5 g, 0.25 mol, 89% pure) in 95% EtOH (227 mL). After addition, the mixture was stirred and cooled down to 0° C. at the rate of less than 5° C. per hour. The suspension was then stirred at 0° C. for 2 hours, the solid was collected by vacuum filtration.

The crude solid with 86% ee was dissolved in 95% ethanol (165 mL) at 60° C. The solution was cooled slowly to 20° C. and stirred at this temperature for 18 hours. The solid was collected by vacuum filtration to yield the product as a white granular solid with 99.5% ee.

mp 145.6-147.0° C.

Optical rotation: $[\alpha]^{20}_D = -22.8$ (c 1.0, MeOH).

$^1$H NMR (300 MHz, DMSO-d$^6$) δ 7.26 (m, 3H), 6.62 (m, 4H), 4.35 (q, J=6.8 Hz, 1H), 3.14 (m, 2H), 3.74 (p, J=7.2 Hz, 1H), 2.87 (dd, J=6.7 Hz, 16.3 Hz, 2H), 2.76 (q, J=7.3 Hz, 2H), 1.36 (s, 9H), 1.35 (s, 6H), 1.34 (d, J=6.8 Hz, 3H), 1.10 (t, J=7.3 Hz, 3H).

$^{13}$C NMR (300 MHz, DMSO-d$^6$) δ 175.8, 172.4, 151.5, 151.2, 142.3, 141.3, 135.5, 132.9, 129.4, 125.0, 115.9, 115.7, 80.7, 74.8, 57.4, 51.2, 41.0, 36.4, 27.8, 26.1, 19.3, 12.3.

FTIR (KBr): 2980, 2934, 1717, 1629, 1576, 1510, 1458, 1405, 1368, 1279, 1257, 1230, 1148, 1121, 1101, 1044, 848, 830, 801, 758, 679, 643, 525 cm$^{-1}$

Elemental Analysis for $C_{28}H_{39}NO_6S \cdot 0.43$ EtOH:
Calculated: C, 64.19; H, 7.66; N, 2.13, S: 5.49. Found: C, 64.12; H, 7.87; N, 2.18, S: 5.89.

EXAMPLE 8

(R)-(−)-tert-Butyl 2-(2-ethylamino-indan-5-ylsulfanyl)-2-methyl-propionate

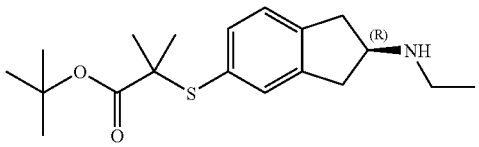

The diastereomeric salt prepared in Example 7 above (357 g, 0.635 mol) was charged into a mixture of isopropyl acetate (2 L) and 50% of NaOH (102 g, 1.28 mol) in water (0.8 L). The mixture was stirred until all solids dissolved. After removal of the bottom aqueous layer, the isopropyl acetate layer was washed with water 3 times until the pH of the aqueous phase was about 7. The organic solution was concentrated at 60° C. to remove about ¾ of the isopropyl acetate. 1 L of fresh isopropyl acetate was added and the amount of residual water in the solution was assayed by KF. The solution was used for the next step directly.

An analytical sample was obtained as clear oil by simple concentration of a small amount of the crude solution.

Optical Rotation: $[\alpha]^{20}{}_D = -17.1$ (c 1.0, MeOH).

MS (APCI): m/z 336.3 (MH$^+$).

$^1$H NMR (300 MHz, DMSO-d$^6$) δ 7.26 (s, 1H), 7.19 (m, 2H), 3.50 (p, J=6.8 Hz, 1H), 3.04 (dt, J=16 Hz, 6.5 Hz, 2H), 2.64 (m, 2H), 2.57 (q, J=7.0 Hz, 2H), 1.36 (s, 9H), 1.34 (s, 6H), 1.01 (t, J=7.0 Hz, 3H).

$^{13}$C NMR (300 MHz, DMSO-d$^6$) δ 172.0, 143.8, 142.8, 134.5, 132.6, 128.2, 124.6, 80.2, 59.2, 50.7, 41.7, 39.3, 27.4, 25.7, 15.2.

FTIR (ReactIR, neat): 2971, 2933, 2838, 1721, 1474, 1461, 1385, 1366, 1343, 1275, 1256, 1146, 1121, 1036, 1009, 942, 847, 820, 752, 706 cm$^{-1}$.

Elemental Analysis for $C_{19}H_{29}NO_2S$:
Calculated: C, 68.02; H, 8.71; N, 4.17; S, 9.56. Found: C, 67.94, H, 8.93; N, 4.09, S, 9.54.

EXAMPLE 9

(R)-(+)-tert-Butyl 2-{2-[1-ethyl-3-(4-trifluoromethoxy-phenyl)-ureido]-indan-5-ylsulfanyl}-2-methyl-propionate

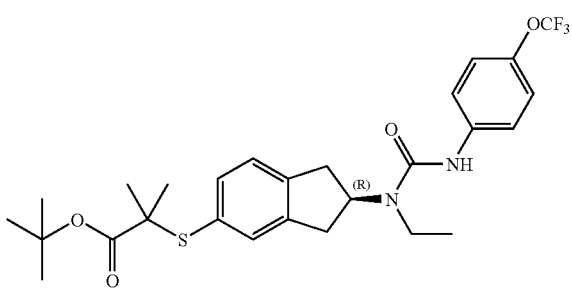

To a solution of tert-butyl 2-(2-ethylamino-indan-5-ylsulfanyl)-2-methyl-propionate (182 g, 0.544 mol) was added 4-(trifluoromethoxy)phenyl isocyanate (115 g, 0.556 mol) and the reaction temperature was maintained at about 15-20° C. After addition, the clear solution was stirred for 15 minutes at about 15-20° C. The solution was used for the next step directly.

An analytical sample was obtained as a white solid by simple concentration of a small amount of the crude solution.

mp 95.4-97.8° C.

Optical rotation: $[\alpha]^{20}{}_D = +3.4$ (c 1.0, MeOH).

MS (APCI): m/z 280.2 (30%), 306.2 (100%), 437.3 (50%), 483.1 (20%).

$^1$H NMR (300 MHz, DMSO-d$^6$) δ 8.48 (s, 1H), 7.61 (d, J=9.2 Hz, 2H), 7.27 (m, 5H), 4.91 (p, J=8.2 Hz, 1H), 3.37 (q, J=6.8 Hz, 2H), 3.08 (m, 4H), 1.38 (s, 9H), 1.36 (s, 6H), 1.09 (t, J=6.8 Hz, 3H).

$^{13}$C NMR (300 MHz, DMSO-d$^6$) δ 15.5, 26.1, 27.8, 36.6, 38.4, 51.2, 56.8, 80.7, 120.6 (q, J=225 Hz, OCF$_3$), 121.4, 121.5, 124.9, 129.1, 132.8, 135.3, 140.2, 142.3, 143.0, 143.3, 154.9, 172.5,

FTIR (KBr): 3297, 2974, 2933, 1724, 1636, 1605, 1511, 1419, 1369, 1270, 1229, 1198, 1148, 1122, 845, 817, 756, 561 cm$^{-1}$.

Elemental Analysis for $C_{27}H_{33}F_3N_2O_4S$:
Calculated: C, 60.21; H, 6.18; N, 5.20; F, 10.58; S, 5.95. Found: C, 59.87; H, 6.22; N, 5.08; F, 10.86; S, 5.94.

EXAMPLE 10

(R)-(+)-2-{2-[1-Ethyl-3-(4-trifluoromethoxy-phenyl)-ureido]-indan-5-ylsulfanyl}-2-methyl-propionic acid

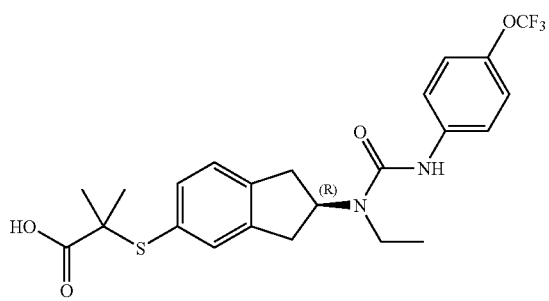

To a solution of tert-butyl 2-{2-[1-ethyl-3-(4-trifluoromethoxy-phenyl)-ureido]-indan-5-ylsulfanyl}-2-methyl-propionate (288 g, 0.534 mol) was added a solution of sulfuric acid (535 g, 5.34 mol) in isopropyl acetate (0.7 L) while maintaining the reaction temperature at about 15-20° C. The clear solution was stirred at 15° C. for 1 hour after the addition. To the reaction mixture was added cold water (0.94 L). After removal of the acidic aqueous layer, the isopropyl acetate layer was washed until the pH of the aqueous layer reached 3. The solution was used in the next step without isolation.

An analytical sample was obtained as a white foam by simple concentration of a small amount of the crude solution.

mp 57° C.

Optical rotation: $[\alpha]^{20}{}_D = +7.7$ (c 1.0, MeOH).

MS (APCI): m/z: 483.1 (MH$^+$).

$^1$H NMR (300 MHz, DMSO-d$^6$) δ 12.43 (br s, 1H), 8.49 (s, 1H), 7.61 (d, J=9.5, 2H), 7.27 (m, 5H), 4.91 (p, J=8.4 Hz, 1H), 3.39 (m, 2H), 3.08 (m, 4H), 1.38 (s, 6H), 1.10 (t, J=6.9 Hz, 3H).

$^{13}$C NMR (300 MHz, DMSO-d$^6$) δ 175.2, 154.9, 143.2, 143.0, 142.3, 140.2, 135.1, 132.6, 129.4, 125.0, 121.5, 121.3, 120.6 (q, J=255 Hz, OCF$_3$), 56.8, 51.0, 38.4, 36.5, 26.0, 15.5.

FTIR (KBr): 3395, 2977, 2935, 1703, 1641, 1511, 1420, 1265, 1200, 1161, 1016, 841, 815, 755 cm$^{-1}$.

Elemental Analysis for C$_{23}$H$_{25}$F$_3$N$_2$O$_4$S:

Calculated: C, 57.25; H, 5.22; N, 5.81; F, 11.81; S, 6.65.
Found: C, 57.00; H, 5.47; N, 5.41; F, 11.75; S, 6.23.

EXAMPLE 11

(R)-(+)-2-{2-[1-Ethyl-3-(4-trifluoromethoxy-phenyl)-ureido]-indan-5-ylsulfanyl}-2-methyl-propionic acid, N,N'-dibenzylethylenediamine salt

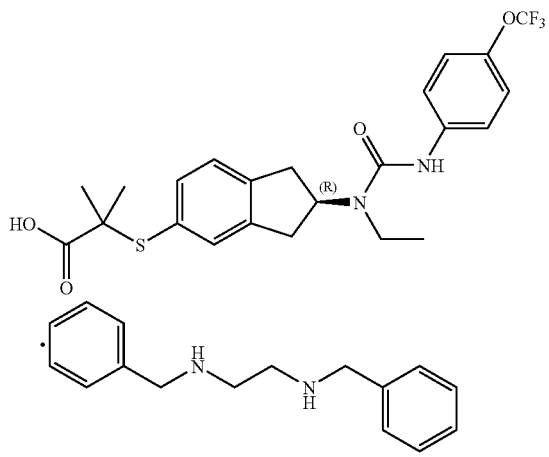

Seeds Preparation:

N,N'-Dibenzylethylenediamine (0.26 g, 1.08 mmol) was added to t-butyl methyl ether solution of 2-{2-[1-ethyl-3-(4-trifluoromethoxy-phenyl)-ureido]-indan-5-ylsulfanyl}-2-methyl-propionic acid (0.52 g, 1.08 mmol). iPrOAc was added to the resulted cloudy solution. The solution was kept in the refrigerator overnight (~20 hours). The solids precipitated were collected by filtration. $^1$H NMR analysis and the melting point measurement of the isolated solids confirmed the formation of the salt with 1:1 mole ratio of acid and N,N'-dibenzylethylenediamine.

Salt Preparation:

A solution of 2-{2-[1-ethyl-3-(4-trifluoromethoxy-phenyl)-ureido]-indan-5-ylsulfanyl}-2-methyl-propionic acid (218.51 g, 0.453 mol) in isopropyl acetate (859 mL) was cooled to about −5 to 0° C. and N,N'-dibenzylethylenediamine (112 g, 0.453 mol) was added over 1 hour. The internal reaction temperature was maintained under 0° C. Heptane (513 mL) was added to the solution until the solution became cloudy. The seeds were added while stirring. The cloudy mixture changed to a uniform suspension within one hour. Additional heptane (60 mL) was then added. After stirred for 1 h, more heptane (180 mL) was added. The suspension was stirred overnight (18 hours) at 0° C.

The solid was filtered and rinsed with a chilled mixture of iPrOAc/heptane (½, 90 mL). The solid was air-dried at the ambient temperature overnight to yield a solid with 99.1% ee.

mp 99-102° C.

Optical rotation: [α]$^{20}_D$=+7.7 (c 1.0, MeOH).

MS (APCI): m/z 483.8 (MH$^+$).

$^1$H NMR (300 MHz, DMSO-d$^6$) δ 8.54 (s, 1H), 7.63 (m, 2H), 7.28 (m, 15H), 6.99 (br s, 3H), 4.91 (p, J=8.5 Hz, 1H), 3.80 (s, 4H), 3.37 (q, J=6.9 Hz, 2H), 3.05 (d, J=7.6 Hz, 4H), 2.77 (s, 4H), 1.33 (s, 6H), 1.09 (t, J=6.9 Hz, 3H).

$^{13}$C NMR (300 MHz, DMSO-d$^6$) δ 176.6, 154.9, 142.9, 142.1, 141.9, 140.3, 138.8, 134.7, 132.2, 131.3, 128.8, 128.5, 127.4, 124.7, 121.4, 121.4, 120.2 (q, J=255 Hz, OCF$_3$), 56.8, 52.9, 52.2, 46.7, 38.3, 36.5, 36.4, 27.3, 15.5.

FTIR (KBr): 3310(broad), 2972, 2849, 1638, 1606, 1539, 1510, 1458, 1418, 1389, 1351, 1264, 1244, 1199, 1162, 842, 816, 748, 698.81, 668 cm$^{-1}$.

Elemental Analysis for C$_{39}$H$_{45}$F$_3$N$_4$O$_4$S:

Calculated: C, 64.80; H, 6.27; N, 7.75; F 7.88; S, 4.44.
Found: C, 64.65; H, 6.35; N, 7.61; F, 8.12, S, 4.51.

EXAMPLE 12

(S)-(+)-tert-Butyl 2-(2-ethylamino-indan-5-ylsulfanyl)-2-methyl-propionate, (S)-(−)-2-(4-hydroxyphenoxy)propionic acid salt

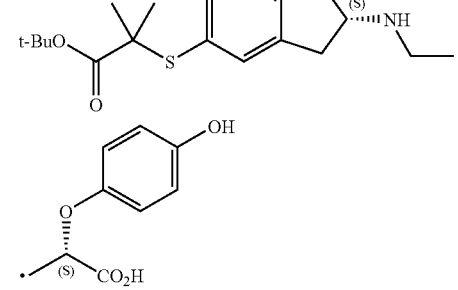

Racemic tert-Butyl 2-(2-ethylamino-indan-5-ylsulfanyl)-2-methyl-propionate (0.30 mmol) and (S)-(−)-2-(4-hydroxyphenoxy)propionic acid (0.30 mmol) were mixed into THF (2 mL) and heated to 50° C. to a clear solution. The reaction mixture was then cooled to the ambient temperature and stirred overnight. White crystalline solid precipitated and determined to be the enriched diastereomeric salt (S)-(+)-tert-Butyl 2-(2-ethylamino-indan-5-ylsulfanyl)-2-methyl-propionate and (S)-(−)-2-(4-hydroxyphenoxy)propionic acid at 48% ee by chiral HPLC.

EXAMPLE 13

(S)-(+)-tert-Butyl 2-(2-ethylamino-indan-5-ylsulfanyl)-2-methyl-propionate, (S)-(−)-2-(4-hydroxyphenoxy)propionic acid salt

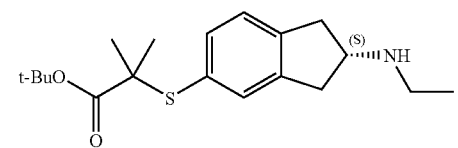

-continued

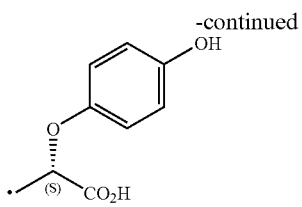

Racemic tert-Butyl 2-(2-ethylamino-indan-5-ylsulfanyl)-2-methyl-propionate (17 g, 51 mmol) and (S)-(−)-2-(4-hydroxyphenoxy)propionic acid (4.6 g, 25 mmol) were dissolved in acetone (55 mL), each separately. The solutions were then mixed and stirred at the ambient temperature overnight. The resulting thick suspension was heated to 55° C. for 6 h, 40° C. for 18 h, then heated to 50° C. and filtered to yield a solid which was determined to be enriched with the diastereomeric salt (S)-(+)-tert-Butyl 2-(2-ethylamino-indan-5-ylsulfanyl)-2-methyl-propionate and (S)-(−)-2-(4-hydroxyphenoxy)propionic at 22% ee. The enriched salt was re-crystallized from acetone twice, to yield the title compound salt (S,S) salt in 94% ee.

$^1$H NMR for 94% ee sample (300 MHz, DMSO-d$^6$) δ 7.26 (m, 3H), 6.62 (m, 4H), 4.35 (q, J=6.8 Hz, 1H), 3.14 (m, 2H), 3.74 (p, J=7.2 Hz, 1H), 2.87 (dd, J=6.7 Hz, 16.3 Hz, 2H), 2.76 (q, J=7.3 Hz, 2H), 1.36 (s, 9H), 1.35 (s, 6H), 1.34 (d, J=6.8 Hz, 3H), 1.10 (t, J=7.3 Hz, 3H).

m.p. for 80% ee sample isolated after first recrystallization as described above: 157-159° C. (DSC)

EXAMPLE 14

2-{6-[1-Ethyl-3-(4-trifluoromethoxyphenyl)ureido]-3-methoxy-5,6,7,8-tetrahydronaphthale-2-ylsulfanyl}-2-methylpropionic acid

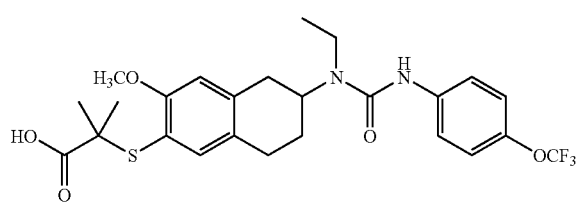

STEP A. 7-Methoxy-1,2,3,4-tetrahydronaphthalen-2-ylamine

To a solution of 7-methoxy-2-tetralone (12.4 g; 70.7 mmol) dissolved in MeOH (350 mL) was added ammonium acetate (82 g; 1.06 mol) and the reaction was stirred for 30 min at room temperature. To the reaction was then added sodium cyanoborohydride (21.5 g; 353 mmol) and the reaction was refluxed for 1 h. Upon completion of the reaction, the reaction was cooled and the solvent removed under reduced pressure. The residue was diluted with EtOAc and 1N NaOH was added to quench the reaction. The aqueous phase was separated and the organic phase washed with H$_2$O, brine, dried over Na$_2$SO$_4$, filtered, and the solvent removed under reduced pressure to yield 7-methoxy-1,2,3,4-tetrahydronapthalen-2-ylamine as a dark oil.

MS, m/z: 178 (M+1) C$_{11}$H$_{15}$NO.

STEP B. N-(7-Methoxy-1,2,3,4-tetrahydronaphthalen-2-yl)-acetamide

To a stirred suspension of 7-methoxy-1,2,3,4-tetrahydronapthalen-2-ylamine (2.54 g; 14.3 mmol) in CH$_2$Cl$_2$ (20 mL) was added DIEA (3.4 mL) and the reaction mixture was cooled to 0° C. Acetyl chloride (1.22 mL; 17.1 mmol) was added dropwise at 0° C. and the reaction was allowed to warm to room temperature, then stirred for 18 h. The reaction mixture was diluted with CH$_2$Cl$_2$, washed with H$_2$O, dried over Na$_2$SO$_4$, filtered and the solvent removed under reduced pressure to yield a crude solid. Purification by flash chromatography (SiO$_2$) eluting with hexanes-EtOAc yielded N-(7-methoxy-1,2,3,4-tetrahydronaphthalen-2-yl)-acetamide as a white solid.

MS, m/z: 220 (M+1) C$_{13}$H$_{17}$NO$_2$.

STEP C. 6-Acetylamino-3-methoxy-5,6,7,8-tetrahydronaphthalene-2-sulfonyl chloride To chlorosulfonic acid (15 mL), cooled to −10° C. was added N-(7-methoxy-1,2,3,4-tetrahydronaphthalen-2-yl)-acetamide (1.44 g; 6.6 mmol). The reaction mixture was stirred at −10° C. for 15 min and quenched carefully by pouring over ice-water. The aqueous phase was extracted with CH$_2$Cl$_2$ (3×), the organic extracts combined, dried over Na$_2$SO$_4$, filtered and evaporated under reduced pressure to yield 6-acetylamino-3-methoxy-5,6,7,8-tetrahydronaphthalene-2-sulfonyl chloride as a white solid.

$^1$H NMR (300 MHz, CDCl$_3$): δ 7.68 (s, 1H), 6.78 (s, 1H), 5.53-5.56 (m, 1H), 4.22-4.31 (m, 1H), 4.00 (s, 3H), 3.18-3.26 (dd, 1H), 2.86-2.90 (m, 2H), 2.67-2.76 (dd, 1H), 2.04-2.12 (m, 1H), 2.00 (s, 1H), 1.73-1.82 (m, 2H).

MS, m/z: 318 (M+1) C$_{13}$H$_{16}$ClNO$_4$S.

STEP D. N-(6-Mercapto-7-methoxy-1,2,3,4-tetrahydronaphthalen-2yl)acetamide

To a suspension of zinc dust (1.16 g; 17.7 mmol) and dimethylsilyl dichloride (2.4 mL; 17.7 mmol) in MeCN (40 mL) was added a solution of 6-acetylamino-3-methoxy-5,6,7,8-tetrahydronaphthalene-2-sulfonyl chloride (1.13 g; 3.55 mmol) in MeCN/DCE (40/10 mL), at room temperature. The reaction suspension was then heated at 81° C. for 4 h, cooled to room temperature, filtered and the solvent evaporated under reduced pressure. The crude residue was purified by reverse-phase semi-prep HPLC eluting with a MeCN—H$_2$O gradient to yield N-(6-mercapto-7-methoxy-1,2,3,4-tetrahydronaphthalen-2-yl)acetamide as a white solid and N-[6-(6-acetylamino-3-methoxy-5,6,7,8-tetrahydronaphthalen-2-yldisulfanyl)-7-methoxy-1,2,3,4,-tetrahydronaphthalen-2-yl]acetamide as a tan solid.

MS, m/z: 252 (M+1; S—H) C$_{13}$H$_{17}$NO$_2$S & 501 (M+1; S—S) C$_{26}$H$_{32}$N$_2$O$_4$S$_2$.

STEP E. 2-(6-Acetylamino-3-methoxy-5,6,7,8-tetrahydronaphthalen-2-ylsulfanyl)-2-methylpropionic acid tert-butyl ester To a suspension of N-[6-(6-acetylamino-3-methoxy-5,6,7,8-tetrahydronaphthalen-2yldisulfanyl)-7-methoxy-1,2,3,4,-tetrahydronaphthalen-2-yl]acetamide (0.368 g; 0.73 mmol) in MeOH (10 mL) was added DMF (3 mL), K$_2$CO$_3$ (0.31 g; 2.26 mmol), tert-butyl 2-bromoisobutyrate (0.66 mL; 2.95 mmol) and NaBH$_4$ (0.28 g; 7.34 mmol) and the reaction mixture was stirred for 18 h at room temperature. The reaction mixture was partitioned between EtOAc and H$_2$O, the aqueous phase extracted with EtOAc, the organic extracts combined, washed with H$_2$O, brine, dried over Na$_2$SO$_4$, filtered and the solvent removed under reduced pressure to yield a crude oil, which was purified by reverse-phase semi-prep HPLC eluting with a MeCN—H$_2$O gradient to yield 2-(6-acetylamino-3-methoxy-5,6,7,8-tetrahydronaphthalen-2-yl-sulfanyl)-2-methylpropionic acid tert-butyl ester as an oil.

MS, m/z: 338 (M+1) C$_{21}$H$_{31}$NO$_4$S.

STEP F. 2-(6-Ethylamino-3-methoxy-5,6,7,8-tetrahydronaphthalen-2-ylsulfanyl)-2-methylpropionic acid tert-butyl ester To a solution of 2-(6-acetylamino-3-methoxy-5,6,7,8-tetrahydronaphthalen-2-ylsulfanyl)-2-methylpropionic acid tert-butyl ester (0.68 g; 1.74 mmol) in THF (15 mL) was added a solution of 1.0 M borane-THF (15 mL), dropwise at room temperature. The reaction mixture was allowed to stir for 18 h at room temperature, then carefully quenched with MeOH (10 mL) and the solvent evaporated under reduced pressure. The residual oil was further azeotroped with MeOH (3×) to yield a mixture of 2-(6-ethylamino-5,6,7,8-tetrahydronaphthalen-2-ylsulfanyl)-2-methylpropionic acid tert-butyl ester and it's borane complex as an oil.

MS, m/z: 380 (M+1) C$_{21}$H$_{33}$NO$_3$S.

STEP G. 2-{6-[1-Ethyl-3-(4-trifluoromethoxyphenyl)ureido]-3-methoxy-5,6,7,8-tetrahydronaphthalen-2-ylsulfanyl}-2-methylpropionic acid tert butyl ester To a mixture of 2-(6-ethylamino-5,6,7,8-tetrahydro-naphthalen-2-ylsulfanyl)-2-methylpropionic acid tert-butyl ester and borane complex (0.054 g; 0.141 mmol) dissolved in CH$_2$Cl$_2$ (2 mL) was added 4-trifluoromethoxyphenyl isocyanate (0.063 mL; 0.284 mmol) and the reaction mixture as stirred at room temperature for 18 h. The solvent was removed under reduced pressure and the crude residue was purified by reverse-phase semi-prep HPLC eluting with a MeCN—H$_2$O gradient to yield 2-{6-[1-ethyl-3-(4-trifluoromethoxyphenyl)ureido]-3-methoxy-5,6,7,8-tetrahydronaphthalen-2-ylsulfanyl}-2-methylpropionic acid tert butyl ester as an oil.

MS, M/Z: 527 ((M-C$_4$H$_8$)+1) C$_{29}$H$_{37}$F$_3$N$_2$O$_5$S.

STEP H. 2-{6-[1-Ethyl-3-(4-trifluoromethoxyphenyl)ureido]-5,6,7,8-tetrahydronaphthalen-2-ylsulfanyl}-2-methylpropionic acid To 2-{6-[1-ethyl-3-(4-trifluoromethoxyphenyl)ureido]-3-methoxy-5,6,7,8-tetrahydronaphthalen-2-ylsulfanyl}-2-methylpropionic acid tert butyl ester (0.02 g; 0.03 mmol) dissolved in CH$_2$Cl$_2$ (1.5 mL) was added TFA (1.5 mL) and the reaction mixture was stirred at room temperature for 1.5 h. The solvent was removed under reduced pressure and the residue was purified by reverse-phase semi-prep HPLC eluting with a MeCN—H$_2$O gradient to yield 2-{6-[1ethyl-3-(4-trifluoromethoxyphenyl)ureido]-5,6,7,8-tetrahydronaphthalen-2-ylsulfanyl}-2-methylpropionic acid as a white solid.

$^1$H NMR (300 MHz, CD$_3$OD): δ 7.45-7.48 (d, 2H), 7.15-7.18 (m, 3H), 6.71 (s, 1H), 4.43-4.79 (m, 1H), 3.75 (s, 3H), 3.43-3.45 (m, 2H), 2.88-3.08 (m, 4H), 1.99-2.03 (m, 2H), 1.38 (s, 6H), 1.25-1.52 (t, 3H).

MS, m/z: 526 (M+1) C$_{25}$H$_{29}$F$_3$N$_2$O$_5$S.

The following compounds were similarly prepared according to the procedure described in Example 14 above with selection and substitution of suitable reagents and reaction conditions.

EXAMPLE 15

2-{6-[3-(4-tert-Butylphenyl)1-ethylureido]-3-methoxy-5,6,7,8-tetrahydronaphthalen-2-ylsulfanyl}-2-methylpropionic acid

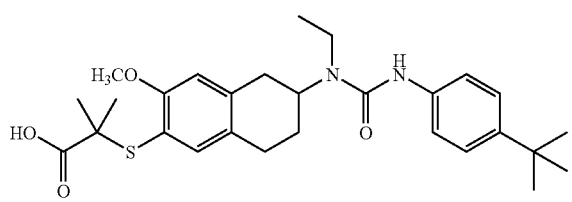

Prepared as an oil by replacing 4-trifluoromethoxyphenyl isocyanate with 4-tert-butylphenyl isocyanate in Step G above.

MS, m/z: 499 (M+1) C$_{28}$H$_{38}$N$_2$O$_4$S.

EXAMPLE 16

2-{6-[1-Ethyl-3-(4-trifluoromethoxyphenyl)ureido]-3-fluoro-5,6,7,8-tetrahydronaphthalen-2-ylsulfanyl}-2-methylpropionic acid

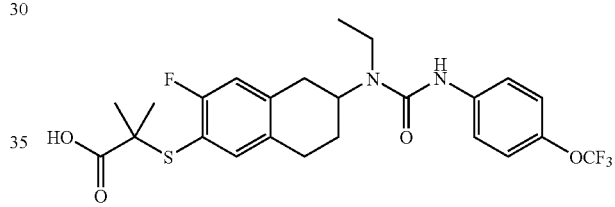

Prepared as a white solid by substituting 7-methoxy-2-tetralone with 7-fluoro-2-tetralone in STEP A above.

$^1$H NMR (300 MHZ, CDCL$_3$): δ 7.46-7.51 (M, 2H), 7.25-7.28 (D, 1H), 7.17-7.20 (D, 2H), 6.92-6.95 (D, 1H), 4.43 (M, 1H), 3.42-3.49 (M, 2H), 2.90-3.11 (M, 4H), 2.02-2.07 (M, 2H), 1.45 (S, 6H), 1.25-1.31 (T, 3H).

MS, m/z: 515 (M+1) C$_{24}$H$_{26}$F$_4$N$_2$O$_4$S.

EXAMPLE 17

2-{6-[1-Ethyl-3-(4-trifluoromethoxyphenyl)ureido]-3-chloro-5,6,7,8-tetrahydronaphthalen-2-ylsulfanyl}-2-methylpropionic acid

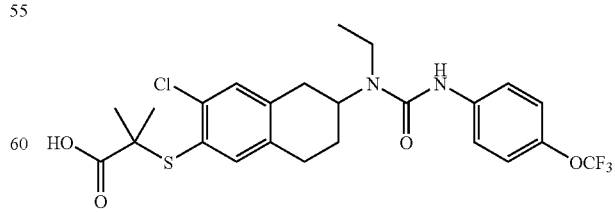

Prepared as a white solid by substituting 7-methoxy-2-tetralone with 7-chloro-2-tetralone in STEP A above.

MS, m/z: 532 (M+1) C$_{24}$H$_{26}$ClF$_3$N$_2$O$_4$S.

EXAMPLE 18

2-{6-[1-Ethyl-3-(4-trifluoromethoxyphenyl)ureido]-3-bromo-5,6,7,8-tetrahydronaphthalen-2-ylsulfanyl}-2-methylpropionic acid

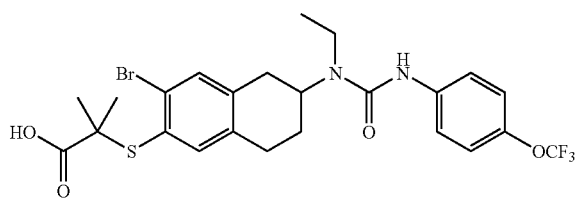

Prepared as a white solid by substituting 7-methoxy-2-tetralone with 7-bromo-2-tetralone in STEP A above.

$^1$H NMR (300 MHz, CDCl$_3$): δ 7.45-7.48 (m, 3H), 7.36 (s, 1H), 7.15-7.18 (d, 2H), 4.41-4.79 (m, 1H), 3.40-3.47 (m, 2H), 2.90-3.07 (m, 4H), 2.01-2.03 (m, 2H), 1.45 (s, 6H), 1.24-1.29 (t, 3H).

MS, m/z: 576 (M+1) $C_{24}H_{26}BrF_3N_2O_4S$.

EXAMPLE 19

2-{6-[1-Ethyl-3-(4-trifluoromethoxyphenyl)ureido]-3-methyl-5,6,7,8-tetrahydronaphthalen-2-ylsulfanyl}-2-methylpropionic acid

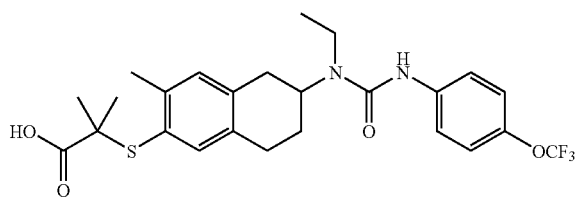

Prepared as a white solid by substituting 7-methoxy-2-tetralone with 7-methyl-2-tetralone in STEP A above.

$^1$H NMR (300 MHz, CDCl$_3$): δ 7.45-7.48 (m, 2H), 7.22 (s, 1H), 7.15-7.18 (d, 2H), 7.02 (s, 1H), 4.41-4.79 (m, 1H), 3.40-3.47 (m, 2H), 2.85-3.03 (m, 4H), 2.39 (s, 3H), 2.01-2.03 (m, 2H), 1.41 (s, 6H), 1.24-1.29 (t, 3H).

MS, m/z: 511 (M+1) $C_{25}H_{29}F_3N_2O_4S$.

EXAMPLE 20

2-{6-[1-Ethyl-3-(4-trifluoromethoxyphenyl)ureido]-3-trifluoromethoxy-5,6,7,8-tetrahydronaphthalen-2-ylsulfanyl}-2-methylpropionic acid

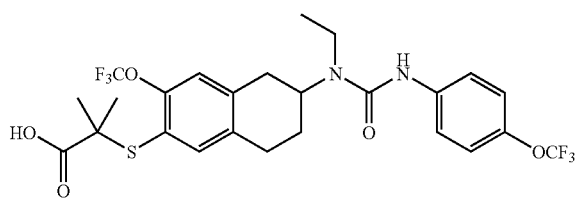

Prepared as white solid by substituting 7-methoxy-2-tetralone with 7-methyl-2-tetralone in STEP A above.

$^1$H NMR (300 MHz, CDCl$_3$): δ 7.45-7.48 (d, 2H), 7.37 (s, 1H), 7.12-7.18 (m, 3H), 4.44 (m, 1H), 3.43-3.48 (m, 2H), 2.97-3.21 (m, 4H), 2.03-2.05 (m, 2H), 1.42 (s, 6H), 1.25-1.30 (t, 3H).

MS, m/z: 580 (M+1) $C_{25}H_{26}F_6N_2O_5S$.

EXAMPLE 21

2-{6-[1-Ethyl-3-(4-trifluoromethoxyphenyl)ureido]-3-phenyl-5,6,7,8-tetrahydronaphthalen-2-ylsulfanyl}-2-methylpropionic acid

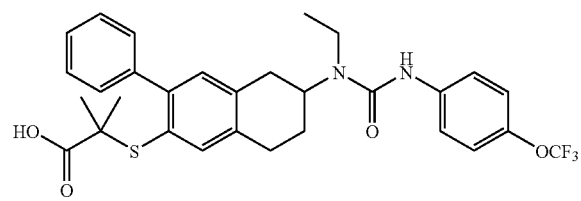

STEP A. 2-{6-Acetylamino-3-phenyl-5,6,7,8-tetrahydronaphthalen-2-ylsulfanyl}-2-methylpropionic acid tert-butyl ester To 2-(6-acetylamino-3-bromo-5,6,7,8-tetrahydronaphthalen-2-ylsulfanyl}-2-methylpropionic acid tert-butyl ester (0.135 g; 0.30 mmol) dissolved in toluene (1.5 mL) was added phenylboronic acid (0.178 g; 1.46 mmol), Pd(PPh$_3$)$_4$ (15 mg; 0.013 mmol) and 2M Na$_2$CO$_3$ (0.61 mL) and the reaction mixture heated at 95° C. for 18 h. The reaction mixture was cooled, diluted with EtOAc, washed with H$_2$O (2×), brine, dried over Na$_2$SO$_4$, filtered and the solvent removed under reduced pressure to yield a crude residue which was purified by flash chromatography (SiO$_2$) eluting with a heptane-EtOAc gradient (50→100%) to yield 2-(6-acetylamino-3-phenyl-5,6,7,8-tetrahydronaphthalen-2-ylsulfanyl}-2-methyl-propionic acid tert-butyl ester as a clear oil.

MS, M/Z: 383 ((M-C$_4$H$_8$)+1) $C_{26}H_{33}NO_3S$

2-{6-[1-Ethyl-3-(4-trifluoromethoxyphenyl)ureido]-3-phenyl-5,6,7,8-tetrahydronaphthalen-2-ylsulfanyl}-2-methylpropionic acid, the compound of Example 21 was additionally prepared, as a white solid, according to the procedure described in Example 14, by selecting and substituting suitable reagents in Steps F, G and H, as appropriate.

$^1$H NMR (300 MHz, CDCl$_3$): δ 7.45-7.48 (d, 2H), 7.29-7.38 (m, 6H), 7.15-7.18 (d, 2H), 7.10 (s, 1H), 4.46 (m, 1H), 3.44-3.49 (m, 2H), 2.98-3.06 (m, 4H), 2.04-2.06 (m, 2H), 1.26-1.30 (t, 3H), 1.14 (s, 6H).

MS, M/Z: 573 (M+1) $C_{25}H_{29}F_3N_2O_5S$

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A crystalline N,N'-dibenzylethylenediamine salt of a compound of formula (IIa)

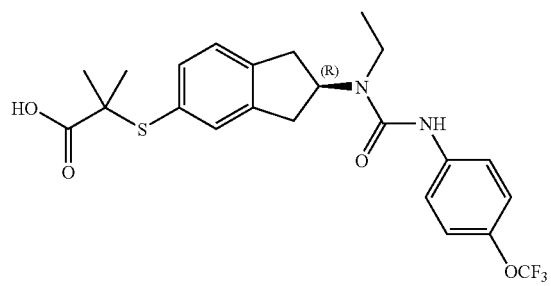

(IIa)

comprising the following X-ray diffraction peaks:

| Position [°2θ] | d-spacing [Å] | Relative Intensity [%] |
|---|---|---|
| 6.3894 | 13.8336 | 17.39 |
| 8.0423 | 10.9938 | 13.38 |
| 12.157 | 7.2803 | 19.22 |
| 16.012 | 5.5354 | 15.74 |
| 17.929 | 4.9475 | 20.77 |
| 18.048 | 4.9151 | 14.20 |
| 19.038 | 4.6618 | 100.00 |
| 19.2656 | 4.6072 | 26.28 |
| 20.325 | 4.3694 | 10.65 |

-continued

| Position [°2θ] | d-spacing [Å] | Relative Intensity [%] |
|---|---|---|
| 21.943 | 4.0508 | 16.85 |
| 22.190 | 4.0063 | 18.63 |
| 22.330 | 3.9815 | 12.37. |

2. A process for the preparation of a N,N'-dibenzylethylenediamine salt of a compound of formula (IIa) as described in claim 1

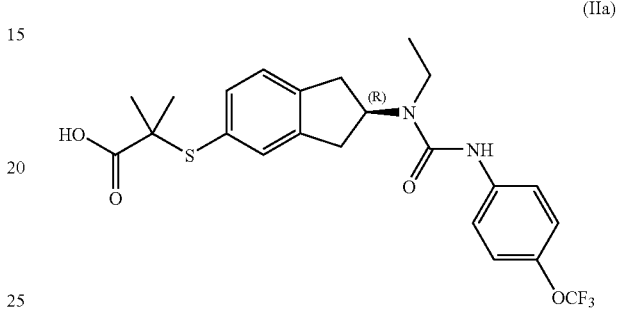

(IIa)

comprising reacting the compound of formula (IIa) with N,N'-dibenzylethylenediamine, in an aprotic solvent.

3. The process of claim 2 wherein the aprotic solvent is isopropyl alcohol.

4. The process of claim 3 wherein the compound of formula (IIa) is reacted with N,N'-dibenzylethylenediaine at a temperature less than about 5° C.

* * * * *